US012654062B2

(12) United States Patent
Remsberg et al.

(10) Patent No.: US 12,654,062 B2
(45) **Date of Patent: \*Jun. 16, 2026**

(54) GAIT DATA COLLECTION AND ANALYTICS SYSTEM AND METHODS FOR OPERATING UNWEIGHTING TRAINING SYSTEMS

(71) Applicant: AlterG, Inc., Fremont, CA (US)

(72) Inventors: Charles D. Remsberg, Mountain View, CA (US); David E. Lieberman, Tracy, CA (US); Michael P. Arnold, Modesto, CA (US)

(73) Assignee: Lifeward CA, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/419,253

(22) Filed: Jan. 22, 2024

(65) Prior Publication Data

US 2024/0342549 A1 Oct. 17, 2024

Related U.S. Application Data

(63) Continuation of application No. 16/756,860, filed as application No. PCT/US2018/056597 on Oct. 18, 2018, now Pat. No. 11,957,954.

(Continued)

(51) Int. Cl.
*A61H 1/02* (2006.01)
*A61B 5/11* (2006.01)
(Continued)

(52) U.S. Cl.
CPC .............. *A63B 22/02* (2013.01); *A61B 5/112* (2013.01); *A61B 5/1123* (2013.01); (Continued)

(58) Field of Classification Search
CPC ............ A63B 21/00181; A63B 21/068; A63B 2225/02; A63B 2225/62; A63B 2230/01; (Continued)

(56) References Cited

U.S. PATENT DOCUMENTS 32,109 A 4/1861 DeBrame
43,972 A 8/1864 Coldwell
(Continued)

FOREIGN PATENT DOCUMENTS

CA 2216216 A 5/1999
CN 2034152 U 3/1989
(Continued)

OTHER PUBLICATIONS

Lillegard, R.; Running on air (retrieved Aug. 10, 2016 from the internet: http://www.lightspeedrunningandrehabilitation.com/in-the-news/running-on-air/#more-89); Duluth Superior Magazine; 3 pgs.; Jul. 2, 2012.

(Continued)

*Primary Examiner* — Lawrence S Galka
(74) *Attorney, Agent, or Firm* — Shay Glenn LLP

(57) ABSTRACT

Described herein are fields of exercise or therapy systems in particular exercise or therapy systems that controllably generate and maintain an unweighted environment using a mechanical system or a differential air pressure (DAP) envelope about a user so as to at least partially or completely unweight the user. This application also relates to improved control systems for pressure chambers for use in differential air pressure (DAP) systems including data collection and utilization for general fitness use, athletic use, or medical use treadmills and related software, control and analytics systems, especially as related to obtaining gait data from load cells provided in the system.

10 Claims, 18 Drawing Sheets

Under treadmill loadcells

Related U.S. Application Data

(60) Provisional application No. 62/574,138, filed on Oct. 18, 2017.

(51) Int. Cl.
| | |
|---|---|
| *A61H 3/00* | (2006.01) |
| *A63B 22/00* | (2006.01) |
| *A63B 22/02* | (2006.01) |
| *A63B 71/06* | (2006.01) |

(52) U.S. Cl.
CPC ........... *A61H 1/0229* (2013.01); *A61H 3/008* (2013.01); *A63B 22/0023* (2013.01); *A63B 71/0622* (2013.01); *A61H 2201/5007* (2013.01); *A61H 2201/5061* (2013.01); *A61H 2201/5071* (2013.01); *A63B 2071/065* (2013.01); *A63B 2220/17* (2013.01); *A63B 2220/18* (2013.01); *A63B 2220/52* (2013.01); *A63B 2225/02* (2013.01)

(58) Field of Classification Search
CPC ...... A63B 2230/015; A63B 2208/0204; A63B 2208/053; A63B 2220/56; A63B 69/0028; A63B 71/0054; A61B 5/112; A61B 2505/09; A61H 1/0229; A61H 3/00; A61H 3/008; A61H 2201/0103; A61H 2201/5071; A61N 1/36003
See application file for complete search history.

(56) References Cited

U.S. PATENT DOCUMENTS

| | | |
|---|---|---|
| 44,198 A | 9/1864 | Jones |
| 54,530 A | 5/1866 | Hadfield |
| 60,883 A | 1/1867 | Hadfield |
| 68,637 A | 9/1867 | Mason |
| 72,631 A | 12/1867 | Hadfield |
| 76,053 A | 3/1868 | Colwell |
| 100,867 A | 3/1870 | Curran |
| 217,918 A | 7/1879 | White |
| 219,439 A | 9/1879 | Blend |
| 458,136 A | 8/1891 | Wilder |
| 823,812 A | 6/1906 | Ritter |
| 871,074 A | 11/1907 | Stockton |
| 1,193,374 A | 8/1916 | Gilliam |
| 1,223,707 A | 4/1917 | Lyon |
| 1,336,774 A | 4/1920 | Cooper |
| 1,504,166 A | 8/1924 | Thornley |
| 1,507,554 A | 9/1924 | Cooper |
| 1,553,520 A | 9/1925 | Dougherty |
| 1,578,852 A | 3/1926 | Schmutzer |
| 1,580,508 A | 4/1926 | Liles |
| 1,586,254 A | 5/1926 | Lovejoy |
| 2,050,500 A | 8/1936 | Osborn |
| 2,108,566 A | 2/1938 | Brooke |
| 2,109,188 A | 2/1938 | Elizaveta |
| 2,327,671 A | 8/1943 | Rupprecht |
| 2,438,979 A | 4/1948 | Lea |
| 2,719,568 A | 10/1955 | Webb |
| 2,785,004 A | 3/1957 | Cooper |
| 2,819,755 A | 1/1958 | Harold et al. |
| 2,871,915 A | 2/1959 | Hogan |
| 2,892,455 A | 6/1959 | Hutton |
| 2,991,523 A | 7/1961 | Conte |
| 3,085,357 A | 4/1963 | Nissen et al. |
| 3,140,869 A | 7/1964 | Pacuk |
| 3,165,314 A | 1/1965 | Clearman et al. |
| 3,176,793 A | 4/1965 | Roland |
| 3,252,704 A | 5/1966 | Louise |
| 3,292,613 A | 12/1966 | Macleod |
| 3,332,176 A | 7/1967 | Knetzer |
| 3,335,529 A | 8/1967 | Gedney |
| 3,353,309 A | 11/1967 | Kwake |
| 3,428,015 A | 2/1969 | Cloud |
| 3,730,587 A | 5/1973 | Bloxham et al. |
| 3,738,027 A | 6/1973 | Schoch |
| 3,747,596 A | 7/1973 | Mills |
| 3,768,467 A | 10/1973 | Jennings |
| 3,778,052 A | 12/1973 | Andow et al. |
| 3,824,994 A | 7/1974 | Soderberg, Sr. |
| 3,911,913 A | 10/1975 | June |
| 4,149,712 A | 4/1979 | Murphy |
| 4,188,966 A | 2/1980 | Palmer et al. |
| 4,205,839 A | 6/1980 | Best |
| 4,211,426 A | 7/1980 | Motloch |
| 4,257,407 A | 3/1981 | Macchi |
| 4,343,302 A | 8/1982 | Dillon |
| 4,411,422 A | 10/1983 | Solloway |
| 4,479,646 A | 10/1984 | Beistegui Chirapozu |
| 4,509,513 A | 4/1985 | Lasley |
| 4,536,163 A | 8/1985 | Schnirch et al. |
| 4,551,108 A | 11/1985 | Bass |
| 4,576,376 A | 3/1986 | Miller |
| 4,614,337 A | 9/1986 | Schönenberger |
| 4,621,621 A | 11/1986 | Marsalis |
| 4,655,447 A | 4/1987 | Dubrinsky et al. |
| 4,712,788 A | 12/1987 | Gaudreau, Jr. |
| 4,731,882 A | 3/1988 | Ekman |
| 4,776,581 A | 10/1988 | Shepherdson |
| 4,805,601 A | 2/1989 | Eischen, Sr. |
| 4,861,021 A | 8/1989 | Edwards et al. |
| 4,863,163 A | 9/1989 | Wehrell |
| 4,887,317 A | 12/1989 | Phillips et al. |
| 4,911,426 A | 3/1990 | Scales |
| 4,921,245 A | 5/1990 | Roberts |
| 4,922,426 A | 5/1990 | Obara et al. |
| 4,934,694 A | 6/1990 | McIntosh |
| 4,941,497 A | 7/1990 | Prather et al. |
| 4,959,047 A | 9/1990 | Tripp, Jr. |
| 4,961,544 A | 10/1990 | Bidoia |
| 4,961,573 A | 10/1990 | Wehrell |
| 4,968,028 A | 11/1990 | Wehrell |
| 4,974,829 A | 12/1990 | Gamow et al. |
| 4,976,623 A | 12/1990 | Owsley |
| 5,000,440 A | 3/1991 | Lynch |
| 5,029,579 A | 7/1991 | Trammel |
| 5,048,836 A | 9/1991 | Bellagamba |
| 5,064,193 A | 11/1991 | Sainte et al. |
| 5,070,816 A | 12/1991 | Wehrell |
| 5,075,902 A | 12/1991 | McReynolds et al. |
| 5,112,045 A | 5/1992 | Mason et al. |
| 5,133,339 A | 7/1992 | Whalen et al. |
| 5,156,549 A | 10/1992 | Wehrell |
| 5,174,590 A | 12/1992 | Kerley et al. |
| 5,176,597 A | 1/1993 | Bryne |
| 5,221,241 A | 6/1993 | Bare |
| 5,242,339 A | 9/1993 | Thornton |
| 5,273,502 A | 12/1993 | Kelsey et al. |
| 5,275,426 A | 1/1994 | Tankersley |
| 5,288,283 A | 2/1994 | Meeker |
| 5,295,929 A | 3/1994 | Weisz |
| 5,348,035 A | 9/1994 | Porter |
| 5,356,361 A | 10/1994 | Watenpaugh |
| 5,360,384 A | 11/1994 | Toensing |
| 5,362,298 A | 11/1994 | Brown et al. |
| 5,368,532 A | 11/1994 | Farnet |
| 5,368,533 A | 11/1994 | Feuer et al. |
| 5,372,561 A | 12/1994 | Lynch |
| 5,391,115 A | 2/1995 | Bessey |
| 5,398,678 A | 3/1995 | Gamow |
| 5,403,253 A | 4/1995 | Gaylord |
| 5,403,270 A | 4/1995 | Schipper |
| 5,435,798 A | 7/1995 | Habing et al. |
| 5,512,029 A | 4/1996 | Barnard et al. |
| 5,526,893 A | 6/1996 | Higer |
| 5,527,242 A | 6/1996 | Gangloff |
| 5,569,129 A | 10/1996 | Seif Naraghi et al. |
| 5,571,062 A | 11/1996 | Saganovsky |
| 5,577,598 A | 11/1996 | Schoenenberger |
| 5,577,984 A | 11/1996 | Bare, II |
| 5,593,368 A | 1/1997 | Checketts |
| 5,601,527 A | 2/1997 | Selkowitz |
| 5,603,677 A | 2/1997 | Sollo |

(56)                References Cited

U.S. PATENT DOCUMENTS

| | | | |
|---|---|---|---|
| 5,623,944 A | 4/1997 | Nashner |
| 5,626,540 A | 5/1997 | Hall |
| 5,662,311 A | 9/1997 | Waedekin et al. |
| 5,662,560 A | 9/1997 | Svendsen et al. |
| 5,667,461 A | 9/1997 | Hall |
| 5,671,822 A | 9/1997 | Phillips |
| 5,688,225 A | 11/1997 | Walker |
| 5,695,432 A | 12/1997 | Soderlund |
| 5,702,323 A | 12/1997 | Poulton |
| 5,704,880 A | 1/1998 | Amatulle |
| 5,704,881 A | 1/1998 | Dudley |
| 5,706,822 A | 1/1998 | Khavari |
| 5,738,612 A | 4/1998 | Tsuda |
| 5,738,616 A | 4/1998 | Robertson |
| 5,788,606 A | 8/1998 | Rich |
| 5,799,652 A | 9/1998 | Kotliar |
| 5,816,983 A | 10/1998 | Dawes et al. |
| 5,830,162 A | 11/1998 | Giovannetti |
| 5,857,944 A | 1/1999 | Cone et al. |
| 5,860,857 A | 1/1999 | Wasastjerna et al. |
| 5,876,311 A | 3/1999 | Coates et al. |
| 5,893,367 A | 4/1999 | Dubats et al. |
| 5,919,119 A | 7/1999 | Bohmer et al. |
| 5,919,419 A | 7/1999 | Majuri |
| 5,921,892 A | 7/1999 | Easton |
| 5,960,480 A | 10/1999 | Neustater et al. |
| 6,027,464 A | 2/2000 | Dahlquist |
| 6,033,344 A | 3/2000 | Trulaske et al. |
| 6,042,537 A | 3/2000 | Kaiser |
| 6,093,024 A | 7/2000 | Sokolowski |
| 6,120,418 A | 9/2000 | Plough |
| 6,128,782 A | 10/2000 | Young et al. |
| 6,146,315 A | 11/2000 | Schonenberger |
| 6,158,389 A | 12/2000 | Wehrell |
| 6,174,268 B1 | 1/2001 | Novak |
| 6,217,493 B1 | 4/2001 | Spletzer |
| 6,223,854 B1 | 5/2001 | Nolz |
| 6,244,379 B1 | 6/2001 | Larson |
| 6,261,205 B1 | 7/2001 | Elefson |
| 6,270,414 B2 | 8/2001 | Roelofs |
| 6,273,844 B1 | 8/2001 | Kelsey et al. |
| 6,280,361 B1 | 8/2001 | Harvey et al. |
| 6,332,290 B1 | 12/2001 | DeLamare |
| 6,332,354 B1 | 12/2001 | Lalor et al. |
| 6,348,025 B1 | 2/2002 | Schönenberger |
| 6,405,685 B1 | 6/2002 | Cox |
| 6,436,009 B1 | 8/2002 | Marucci |
| 6,438,756 B1 | 8/2002 | Colorado |
| 6,482,128 B1 | 11/2002 | Michalow |
| 6,490,733 B1 | 12/2002 | Casaubon |
| 6,494,811 B1 | 12/2002 | Alessandri |
| 6,527,285 B1 | 3/2003 | Calandro, II |
| 6,527,678 B1 | 3/2003 | Wang et al. |
| 6,539,946 B2 | 4/2003 | Weyergans |
| 6,554,747 B1 | 4/2003 | Rempe |
| 6,565,624 B2 | 5/2003 | Kutt et al. |
| 6,578,594 B1 | 6/2003 | Bowen et al. |
| 6,609,054 B2 | 8/2003 | Wallace |
| 6,612,845 B1 | 9/2003 | Macri et al. |
| 6,645,126 B1 | 11/2003 | Martin et al. |
| 6,648,411 B2 | 11/2003 | Julien |
| 6,656,091 B1 | 12/2003 | Abelbeck et al. |
| 6,666,801 B1 | 12/2003 | Michalow |
| 6,666,831 B1 | 12/2003 | Edgerton et al. |
| 6,669,605 B2 | 12/2003 | Scates |
| 6,679,510 B2 | 1/2004 | Perena |
| 6,689,075 B2 | 2/2004 | West |
| 6,742,523 B2 | 6/2004 | Dubats |
| D495,384 S | 8/2004 | Rolfes |
| 6,783,482 B2 | 8/2004 | Oglesby et al. |
| 6,821,233 B1 | 11/2004 | Colombo et al. |
| 6,892,403 B2 | 5/2005 | Liljedahl |
| 6,905,459 B2 | 6/2005 | Humphries, Jr. |
| 6,918,858 B2 | 7/2005 | Watterson et al. |
| 6,932,709 B1 | 8/2005 | Gubitosi et al. |
| 6,935,353 B2 | 8/2005 | Hawkes et al. |
| 6,966,870 B2 | 11/2005 | Lan |
| 6,978,497 B1 | 12/2005 | Takizawa |
| 6,988,951 B1 | 1/2006 | Newman et al. |
| 7,141,007 B2 | 11/2006 | Egger |
| 7,166,064 B2 | 1/2007 | Watterson et al. |
| 7,240,621 B2 | 7/2007 | Chepurny et al. |
| 7,278,958 B2 | 10/2007 | Morgan |
| 7,294,094 B1 | 11/2007 | Howle |
| 7,341,543 B2 | 3/2008 | Dandy |
| 7,381,163 B2 | 6/2008 | Gordon et al. |
| 7,472,964 B2 | 1/2009 | King |
| 7,494,453 B2 | 2/2009 | Wehrell |
| 7,544,172 B2 | 6/2009 | Santos-Munne et al. |
| 7,556,040 B2 | 7/2009 | Meyer et al. |
| 7,572,190 B2 | 8/2009 | Habing |
| 7,572,209 B2 | 8/2009 | Brennan |
| 7,591,795 B2 | 9/2009 | Whalen et al. |
| 7,594,281 B1 | 9/2009 | Stinson et al. |
| 7,608,025 B1 | 10/2009 | Best |
| 7,614,991 B2 | 11/2009 | Fox |
| 7,625,320 B2 | 12/2009 | Wehrell |
| 7,651,450 B2 | 1/2010 | Wehrell |
| 7,666,126 B2 | 2/2010 | Rempe |
| 7,727,076 B2 | 6/2010 | Bapst et al. |
| 7,780,587 B2 | 8/2010 | Thornton et al. |
| 7,785,242 B2 | 8/2010 | Solomon |
| 7,837,597 B2 | 11/2010 | Reyes et al. |
| 7,850,629 B2 | 12/2010 | Ravikumar |
| 7,857,731 B2 | 12/2010 | Hickman et al. |
| 7,862,478 B2 | 1/2011 | Watterson et al. |
| 7,874,223 B2 | 1/2011 | Sugar et al. |
| 7,883,450 B2 | 2/2011 | Hidler |
| 7,887,471 B2 | 2/2011 | McSorley |
| 7,914,420 B2 | 3/2011 | Daly et al. |
| 7,938,756 B2 | 5/2011 | Rodetsky et al. |
| 7,955,219 B2 | 6/2011 | Birrell et al. |
| 7,998,040 B2 | 8/2011 | Kram et al. |
| 8,083,643 B2 | 12/2011 | Ng et al. |
| 8,109,478 B2 | 2/2012 | Tristao |
| 8,152,699 B1 | 4/2012 | Ma et al. |
| 8,172,724 B2 | 5/2012 | Solomon |
| 8,221,293 B2 | 7/2012 | Hoffman et al. |
| 8,235,724 B2 | 8/2012 | Gilley et al. |
| 8,246,354 B2 | 8/2012 | Chu et al. |
| 8,251,863 B2 | 8/2012 | Faulring et al. |
| 8,425,620 B2 | 4/2013 | Johnson et al. |
| 8,447,401 B2 | 5/2013 | Miesel et al. |
| 8,464,716 B2 | 6/2013 | Kuehne et al. |
| 8,470,051 B2 | 6/2013 | Moyer et al. |
| 8,480,602 B1 | 7/2013 | Cook |
| 8,573,612 B1 | 11/2013 | Fulk et al. |
| 8,656,516 B1 | 2/2014 | Reinhardt Rawlings et al. |
| 8,762,167 B2 | 6/2014 | Blander et al. |
| 8,840,572 B2 | 9/2014 | Whalen et al. |
| 8,888,664 B1 | 11/2014 | Butler |
| 8,968,163 B1 | 3/2015 | Vidmar |
| 9,087,454 B2 | 7/2015 | Crivello et al. |
| 9,314,393 B2 | 4/2016 | Kim et al. |
| 9,370,680 B1 | 6/2016 | Macaulay et al. |
| 9,474,934 B1 | 10/2016 | Krueger et al. |
| 9,483,957 B1 | 11/2016 | Fuemmeler |
| 9,642,764 B2 | 5/2017 | Kuehne et al. |
| 9,672,754 B2 | 6/2017 | Yuen et al. |
| 9,713,439 B1 | 7/2017 | Wu et al. |
| 9,914,003 B2 | 3/2018 | Kuehne et al. |
| 10,265,565 B2 | 4/2019 | Jue et al. |
| 10,342,461 B2 | 7/2019 | Basta et al. |
| 10,493,309 B2 | 12/2019 | Jue et al. |
| 11,752,058 B2 | 9/2023 | Kuehne et al. |
| 11,806,564 B2 | 11/2023 | Basta et al. |
| 11,957,954 B2 | 4/2024 | Remsberg et al. |
| 12,171,715 B2 | 12/2024 | Whalen et al. |
| 12,178,772 B2 | 12/2024 | Kuehne et al. |
| 12,226,668 B2 | 2/2025 | Phillips et al. |
| 12,239,595 B2 | 3/2025 | Kuehne et al. |
| 2001/0018564 A1 | 8/2001 | Manor et al. |
| 2002/0010056 A1 | 1/2002 | Borsheim |
| 2002/0022554 A1 | 2/2002 | Borsheim |

(56)                    References Cited

U.S. PATENT DOCUMENTS

| | | |
|---|---|---|
| 2002/0032103 A1 | 3/2002 | Cook |
| 2002/0065173 A1 | 5/2002 | Cook |
| 2003/0032904 A1 | 2/2003 | Egger |
| 2003/0046113 A1 | 3/2003 | Johnson et al. |
| 2003/0204148 A1 | 10/2003 | Lange et al. |
| 2004/0016043 A1 | 1/2004 | Uno et al. |
| 2004/0019304 A1 | 1/2004 | West |
| 2004/0171465 A1 | 9/2004 | Hald et al. |
| 2004/0212240 A1 | 10/2004 | Zwezdaryk |
| 2004/0238285 A1 | 12/2004 | Stokes |
| 2004/0245298 A1 | 12/2004 | Refsum |
| 2004/0249675 A1 | 12/2004 | Stark et al. |
| 2004/0259689 A1 | 12/2004 | Wilkins et al. |
| 2005/0026757 A1 | 2/2005 | Creary |
| 2005/0075680 A1 | 4/2005 | Lowry et al. |
| 2005/0101448 A1 | 5/2005 | He et al. |
| 2005/0183759 A1 | 8/2005 | Wolfe |
| 2005/0250624 A1 | 11/2005 | Yu |
| 2006/0009333 A1 | 1/2006 | Wang |
| 2006/0031984 A1 | 2/2006 | Takizawa |
| 2006/0052728 A1 | 3/2006 | Kerrigan et al. |
| 2006/0062413 A1 | 3/2006 | Wehrell |
| 2006/0079378 A1 | 4/2006 | Ader |
| 2006/0185065 A1 | 8/2006 | Allen |
| 2006/0190051 A1 | 8/2006 | Gerber et al. |
| 2006/0199712 A1 | 9/2006 | Barnard et al. |
| 2006/0240947 A1 | 10/2006 | Qu |
| 2006/0240956 A1 | 10/2006 | Piane |
| 2006/0247104 A1 | 11/2006 | Grabiner et al. |
| 2007/0016116 A1 | 1/2007 | Reinkensmeyer et al. |
| 2007/0054783 A1 | 3/2007 | Egger |
| 2007/0104316 A1 | 5/2007 | Ruchala et al. |
| 2007/0219059 A1 | 9/2007 | Schwartz et al. |
| 2007/0219069 A1 | 9/2007 | Nativ |
| 2007/0272484 A1 | 11/2007 | Helms |
| 2008/0017227 A1 | 1/2008 | Ward |
| 2008/0070757 A1 | 3/2008 | Albert |
| 2008/0109262 A1 | 5/2008 | Dovark et al. |
| 2008/0229495 A1 | 9/2008 | Takizawa |
| 2008/0246581 A1 | 10/2008 | Irie et al. |
| 2008/0281633 A1 | 11/2008 | Burdea et al. |
| 2008/0282442 A1 | 11/2008 | Bauvois |
| 2008/0300118 A1 | 12/2008 | Wehrell |
| 2008/0306412 A1 | 12/2008 | Nieminen et al. |
| 2009/0014004 A1 | 1/2009 | Whalen et al. |
| 2009/0036272 A1 | 2/2009 | Yoo |
| 2009/0047644 A1 | 2/2009 | Mensah et al. |
| 2009/0082700 A1 | 3/2009 | Whalen et al. |
| 2009/0221404 A1 | 9/2009 | Dorogusker et al. |
| 2009/0236176 A1 | 9/2009 | Sheu et al. |
| 2009/0255531 A1 | 10/2009 | Johnson et al. |
| 2009/0269728 A1 | 10/2009 | Verstegen et al. |
| 2010/0000547 A1 | 1/2010 | Johnson et al. |
| 2010/0006737 A1 | 1/2010 | Colombo et al. |
| 2010/0139057 A1 | 6/2010 | Soderberg et al. |
| 2010/0170546 A1 | 7/2010 | Popovic et al. |
| 2010/0197462 A1 | 8/2010 | Piane |
| 2010/0197465 A1 | 8/2010 | Stevenson |
| 2010/0248903 A1 | 9/2010 | Cardile |
| 2010/0279837 A1 | 11/2010 | Stengel |
| 2011/0054946 A1 | 3/2011 | Coulter et al. |
| 2011/0086743 A1 | 4/2011 | Stewart |
| 2011/0098157 A1 | 4/2011 | Whalen et al. |
| 2011/0098615 A1 | 4/2011 | Whalen et al. |
| 2011/0179068 A1 | 7/2011 | O'Brien |
| 2011/0219899 A1 | 9/2011 | Dize et al. |
| 2011/0312473 A1 | 12/2011 | Chu et al. |
| 2012/0004581 A1 | 1/2012 | Dinon |
| 2012/0029666 A1 | 2/2012 | Crowley et al. |
| 2012/0042917 A1 | 2/2012 | Workman et al. |
| 2012/0238921 A1 | 9/2012 | Kuehne et al. |
| 2012/0277643 A1 | 11/2012 | Whalen et al. |
| 2012/0302301 A1 | 11/2012 | Homsi |
| 2013/0095459 A1 | 4/2013 | Tran |
| 2013/0117908 A1 | 5/2013 | Dyson |
| 2013/0325491 A1 | 12/2013 | Ferrari |
| 2014/0026893 A1 | 1/2014 | Johnson et al. |
| 2014/0058312 A1 | 2/2014 | Ziehler et al. |
| 2014/0081661 A1 | 3/2014 | Fu et al. |
| 2014/0113775 A1 | 4/2014 | Egan |
| 2014/0147820 A1 | 5/2014 | Snow et al. |
| 2014/0228985 A1 | 8/2014 | Elliott et al. |
| 2015/0011917 A1 | 1/2015 | Whalen et al. |
| 2015/0181314 A1 | 6/2015 | Swanson |
| 2015/0199494 A1 | 7/2015 | Koduri et al. |
| 2015/0251055 A1 | 9/2015 | Ashby |
| 2015/0325139 A1 | 11/2015 | Kang et al. |
| 2015/0379239 A1 | 12/2015 | Basta et al. |
| 2016/0000155 A1 | 1/2016 | Marecek et al. |
| 2016/0055760 A1 | 2/2016 | Mirabile |
| 2016/0073704 A1 | 3/2016 | Basta et al. |
| 2016/0242993 A1 | 8/2016 | Whalen et al. |
| 2017/0014295 A1 | 1/2017 | Whalen et al. |
| 2017/0027803 A1 | 2/2017 | Agrawal et al. |
| 2017/0128769 A1 | 5/2017 | Long et al. |
| 2017/0367916 A1 | 12/2017 | Kuehne et al. |
| 2019/0046828 A1 | 2/2019 | Kuehne et al. |
| 2019/0099315 A1 | 4/2019 | Kuehne et al. |
| 2019/0099320 A1 | 4/2019 | Whalen et al. |
| 2019/0150530 A1 | 5/2019 | Basta et al. |
| 2019/0255381 A1 | 8/2019 | Bayerlein et al. |
| 2019/0392939 A1 | 12/2019 | Basta et al. |
| 2020/0221975 A1 | 7/2020 | Basta et al. |
| 2020/0384309 A1 | 12/2020 | Long et al. |
| 2021/0187348 A1 | 6/2021 | Phillips et al. |
| 2021/0196552 A1 | 7/2021 | Whalen et al. |
| 2021/0205165 A1 | 7/2021 | Kuehne et al. |
| 2021/0251841 A1 | 8/2021 | Whalen et al. |
| 2022/0059198 A1 | 2/2022 | Basta et al. |
| 2023/0058141 A1 | 2/2023 | Long et al. |
| 2024/0189658 A1 | 6/2024 | Long et al. |
| 2024/0245957 A1 | 7/2024 | Basta et al. |

FOREIGN PATENT DOCUMENTS

| | | | |
|---|---|---|---|
| CN | 2208414 | Y | 9/1995 |
| CN | 202860021 | U | 4/2013 |
| DE | 2623091 | A1 | 11/1977 |
| DE | 29508818 | U1 | 11/1995 |
| DE | 19502801 | C2 | 10/1996 |
| DE | 20004959 | U1 | 6/2000 |
| DE | 20305670 | U1 | 8/2003 |
| DE | 20313772 | U1 | 12/2003 |
| DE | 10362043 | A1 | 5/2005 |
| DE | 102006010887 | A1 | 9/2007 |
| EP | 0917890 | A2 | 5/1999 |
| EP | 2512758 | A2 | 10/2012 |
| EP | 2532927 | A2 | 12/2012 |
| ES | 2151390 | A1 | 12/2000 |
| FR | 1180387 | A1 | 6/1959 |
| FR | 2755865 | A1 | 5/1998 |
| FR | 2831065 | A1 | 4/2003 |
| FR | 2846888 | A1 | 5/2004 |
| FR | 2939050 | A1 | 6/2010 |
| GB | 2128488 | A | 5/1984 |
| GB | 2314512 | A | 1/1998 |
| JP | 59002993 | A | 1/1984 |
| JP | 63109878 | A | 5/1988 |
| JP | 05500760 | A | 2/1993 |
| JP | 05049596 | A | 6/1993 |
| JP | 1022334 | S | 10/1998 |
| JP | 11113988 | A | 4/1999 |
| JP | 2000342713 | A | 12/2000 |
| JP | 2001112886 | A | 4/2001 |
| JP | 2001517187 | A | 10/2001 |
| JP | 200228202 | A | 1/2002 |
| JP | 2002360644 | A | 12/2002 |
| JP | 2004073445 | A | 3/2004 |
| JP | 2004329365 | A | 11/2004 |
| JP | 2004353439 | A | 12/2004 |
| JP | 2005102798 | A | 4/2005 |
| JP | 2007151676 | A | 6/2007 |
| JP | 2008538511 | A | 10/2008 |
| JP | 1395000 | S | 8/2010 |

(56)                    References Cited

FOREIGN PATENT DOCUMENTS

| JP | 1421980 S | 8/2011 |
|----|-----------|--------|
| JP | 2012214936 A | 11/2012 |
| KR | 20030086404 A | 11/2003 |
| TW | 425592 B | 3/2001 |
| TW | I235427 B | 7/2005 |
| TW | M339250 U | 9/2008 |
| WO | WO96/31256 A1 | 10/1996 |
| WO | WO99/30271 A1 | 6/1999 |
| WO | WO01/24900 A1 | 4/2001 |
| WO | WO02/098516 A1 | 12/2002 |
| WO | WO2004/080365 A1 | 9/2004 |
| WO | WO2004/103176 A1 | 12/2004 |
| WO | WO2006/050787 A1 | 5/2006 |
| WO | WO2006/061834 A2 | 6/2006 |
| WO | WO2007/038888 A1 | 4/2007 |
| WO | WO2007/115565 A2 | 10/2007 |
| WO | WO2008/030366 A2 | 3/2008 |
| WO | WO2008/058567 A1 | 5/2008 |
| WO | WO2009/151630 A1 | 12/2009 |
| WO | WO2010/132550 A1 | 11/2010 |
| WO | WO2011/089632 A1 | 7/2011 |
| WO | WO2011/112898 A1 | 9/2011 |
| WO | WO2012/107700 A2 | 8/2012 |
| WO | WO2012/118143 A1 | 9/2012 |
| WO | WO2012/129125 A2 | 9/2012 |
| WO | WO2013/019956 A1 | 2/2013 |
| WO | WO2013/021709 A1 | 2/2013 |
| WO | WO2014/138228 A1 | 9/2014 |
| WO | WO2014/138281 A1 | 9/2014 |
| WO | WO2014/153016 A1 | 9/2014 |
| WO | WO2019/079458 A1 | 4/2019 |
| WO | WO2019/079655 A1 | 4/2019 |
| WO | WO2019/089850 A1 | 5/2019 |

OTHER PUBLICATIONS

Phillips et al.; U.S. Appl. No. 18/319,290 entitled "System for unweighting a user and related methods of exercise," filed May 17, 2023.

Kuehne et al.; U.S. Appl. No. 18/360,662 entitled "Differential air pressure systems and methods of using and calibrating such systems for mobility impaired users," filed Jul. 27, 2023.

Long et al.; U.S. Appl. No. 18/450,961 entitled "Pressure chamber and lift for differential air pressure system with medical data collection capabilities," filed Aug. 16, 2023.

Basta et al.; U.S. Appl. No. 18/476,016 entitled "Method of gait evaluation and training with differential pressure system," filed Sep. 27, 2023.

"Feedback Control System;" The Encyclopedia Americana International Edition; pp. 82-84; Dec. 2003.

Burgess et al.; Overground walking speed changes when subjected to body weight support conditions for nonimpaired and post stroke individuals; J NeuroEng Rehabil.; 7(6); 10 pgs.; Feb. 2010.

Capó-Lugo et al.; Maximum walking speeds obtained using treadmill and overground robot system in persons with post-stroke hemiplegia; J NeuroEng Rehabil.; 9(80); 14 pgs.; Oct. 2012.

Díaz et al.; Lower-Limb Robotic Rehabilitation: Literature Review and Challenges; Hindawi Pub. Corp .; Journal of Robotics; vol. 2011; Art. ID 759764; 11 pgs.; (accepted for publn.) Sep. 2011.

Hamilton; Low-Tech Alternative to AlterG on Market; Runner's World; 2 pgs.; Aug. 16, 2012; (printed from internet: http://www.runnersworld.com/elite-runners/low-tech-alternative-alterg-market).

Hargens et al.; Lower body negative pressure to provide load bearing in space; Aviat Space Environ Med; 62(10); pp. 934-937; Oct. 1991.

Kawai et al.; Rehabilitation apparatus for treadmill walking using lower body positive pressure (Japanese & English abstracts); Aerospace and Environmental Medicine; vol. 44; No. 4; 2007.

Lillegard, R.; Running on air (retrieved Aug. 10, 16 from the internet: http://www.lightspeedrunningandrehabilitation.com/in-the-news/running-on-air/#more-89); Duluth Superior Magazine; 3 pgs.; Jul. 2, 2012.

Long et al.; U.S. Appl. No. 62/024,916 entitled Pressure chamber and lift for differential air pressure system; 23 pages; filed Jul. 15, 2014.

Montion Control Tips; (retrieved from the internet: www.motioncontroltips.com/lead-screws/); 5 pgs; on Dec. 19, 2016.

Pates, K.; Duluth physical therapist develops running aid; (retrieved Aug. 10, 2016 from the internet: http://www.lightspeedrunningandrehabilitation.com/in-the-news/duluth-physical-therapist-develops-running-a id/#more-92); Duluth News Tribune; 3 pgs.; Jul. 25, 2012.

Patton et al.; KineAssist: Design and development of a robotic overground gait and balance therapy device; Top Stroke Rebabil.; 15(2); pp. 131-139; Mar.-Apr. 2008.

Vacu Well Wellness & Beauty; Company History and Vacu Well Power Professional treadmill specifications; printed from website (http://www.vacuwell.com); 3 pgs.; printed Apr. 4, 2012.

Whalen et al.; U.S. Appl. No. 18/946,813 entitled "Systems, methods and apparatus for differential air pressure devices," filed Nov. 13, 2024.

Phillips et al.; U.S. Appl. No. 19/016,486 entitled "System for unweighting a user and related methods of exercise," filed Jan. 10, 2025.

Kuehne et al.; U.S. Appl. No. 19/041,887 entitled "Differential air pressure systems," filed Jan. 30, 2025.

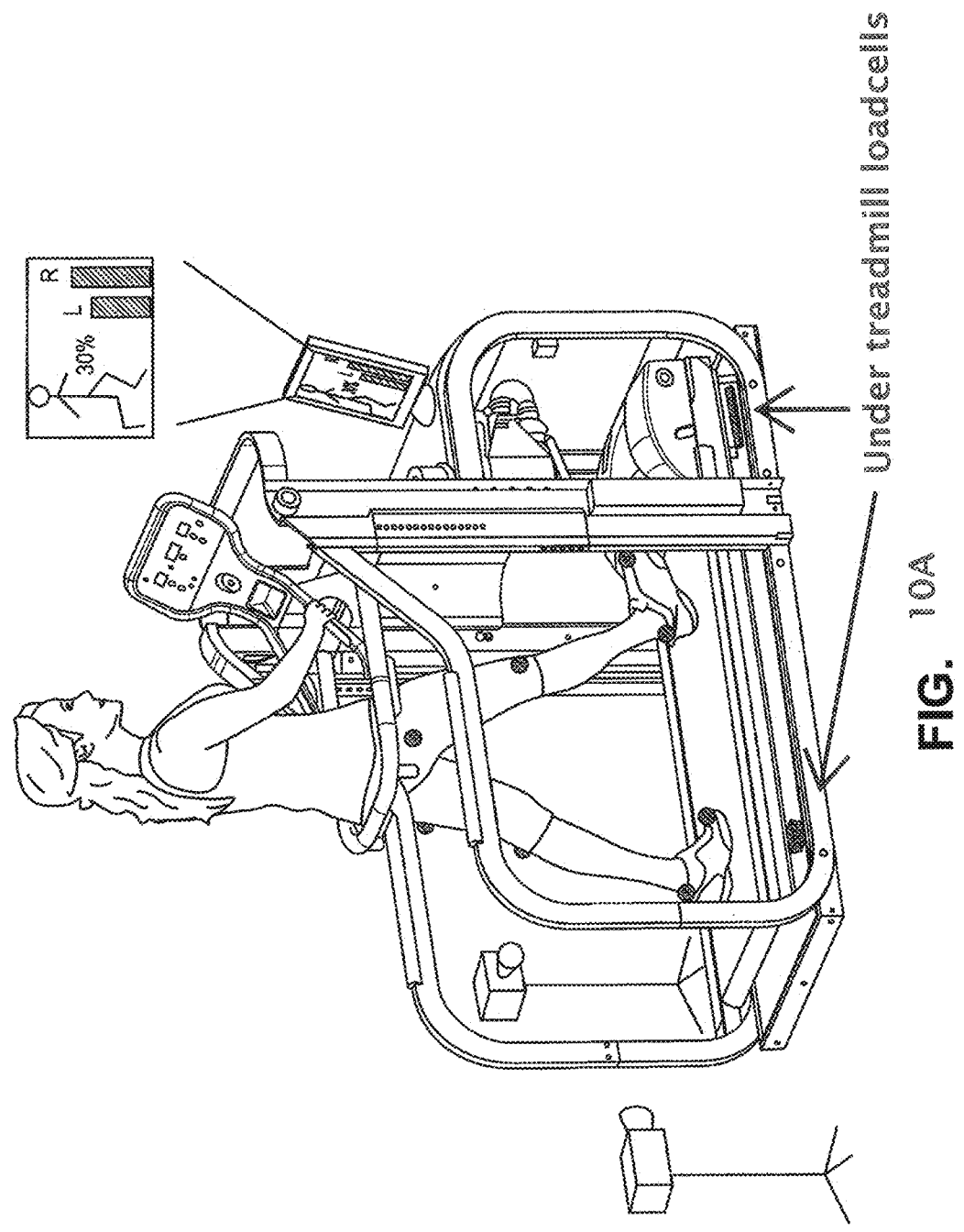
Under treadmill loadcells
FIG. 10A

RECOMMEND ADJUSTMENT TO 75% UNWEIGHTING

Under treadmill loadcells

Exemplary load cell locations

Motor 33 may optionally be within the interior beneath slats 4

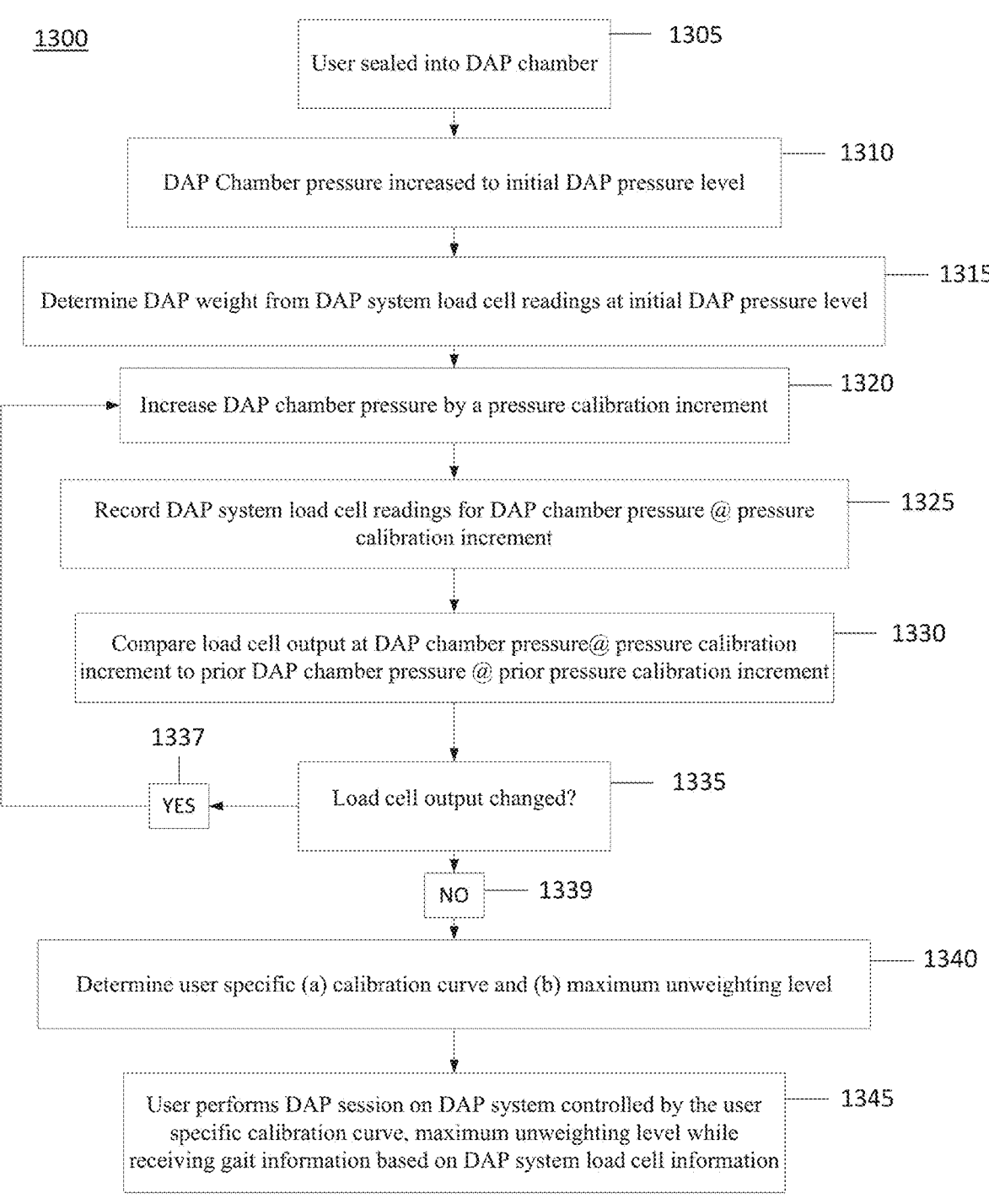

1300

User sealed into DAP chamber — 1305

DAP Chamber pressure increased to initial DAP pressure level — 1310

Determine DAP weight from DAP system load cell readings at initial DAP pressure level — 1315

Increase DAP chamber pressure by a pressure calibration increment — 1320

Record DAP system load cell readings for DAP chamber pressure @ pressure calibration increment — 1325

Compare load cell output at DAP chamber pressure@ pressure calibration increment to prior DAP chamber pressure @ prior pressure calibration increment — 1330

1337

YES

Load cell output changed? — 1335

NO — 1339

Determine user specific (a) calibration curve and (b) maximum unweighting level — 1340

User performs DAP session on DAP system controlled by the user specific calibration curve, maximum unweighting level while receiving gait information based on DAP system load cell information — 1345

FIG. 13

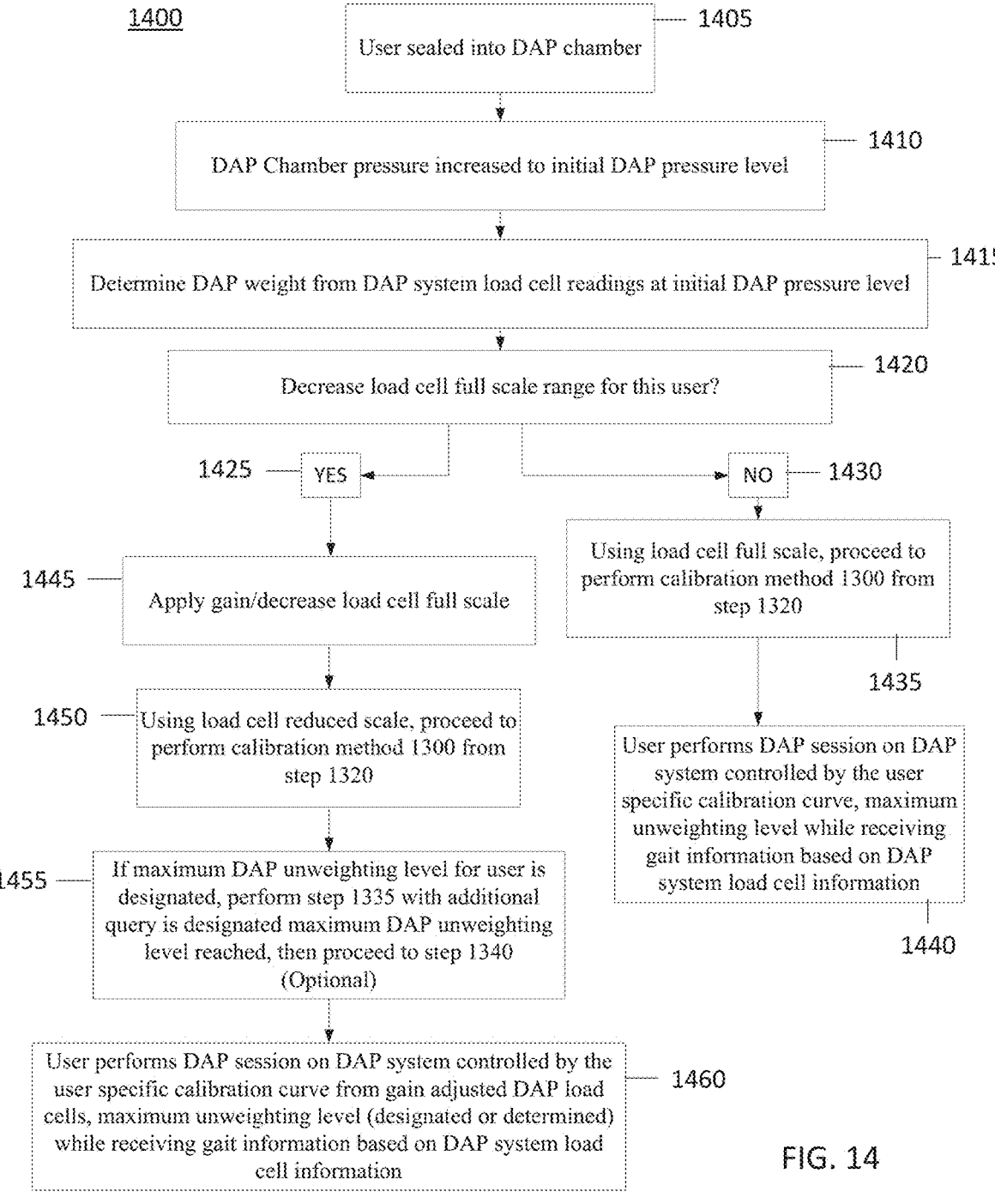

1400

User sealed into DAP chamber — 1405

DAP Chamber pressure increased to initial DAP pressure level — 1410

Determine DAP weight from DAP system load cell readings at initial DAP pressure level — 1415

Decrease load cell full scale range for this user? — 1420

1425 — YES          NO — 1430

1445 — Apply gain/decrease load cell full scale

Using load cell full scale, proceed to perform calibration method 1300 from step 1320

1435

1450 — Using load cell reduced scale, proceed to perform calibration method 1300 from step 1320

User performs DAP session on DAP system controlled by the user specific calibration curve, maximum unweighting level while receiving gait information based on DAP system load cell information

1440

1455 — If maximum DAP unweighting level for user is designated, perform step 1335 with additional query is designated maximum DAP unweighting level reached, then proceed to step 1340 (Optional)

User performs DAP session on DAP system controlled by the user specific calibration curve from gain adjusted DAP load cells, maximum unweighting level (designated or determined) while receiving gait information based on DAP system load cell information — 1460

FIG. 14

GAIT DATA COLLECTION AND ANALYTICS SYSTEM AND METHODS FOR OPERATING UNWEIGHTING TRAINING SYSTEMS

CROSS REFERENCE TO RELATED APPLICATION

This application is a continuation of Ser. No. 16/756,860 filed on Apr. 17, 2020, entitled "GAIT DATA COLLECTION AND ANALYTICS SYSTEM AND METHODS FOR OPERATING UNWEIGHTING TRAINING SYSTEMS," which is the National Stage Entry of International Patent Application No. PCT/2018/056597 filed on Oct. 18, 2018, entitled "GAIT DATA COLLECTION AND ANALYTICS SYSTEM AND METHODS FOR OPERATING UNWEIGHTING TRAINING SYSTEMS," which claims priority to U.S. Provisional Patent Application No. 62/574,138 filed on Oct. 18, 2017 entitled "GAIT DATA COLLECTION AND ANALYTICS SYSTEM AND METHODS FOR OPERATING UNWEIGHTING TRAINING SYSTEMS," each of which is incorporated herein by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This application relates to the field of exercise or therapy systems in particular exercise or therapy systems that controllably generate and maintain an unweighted environment using a mechanical system or a differential air pressure (DAP) envelope about a user so as to at least partially or completely unweight the user. This application also relates to improved control systems for pressure chambers for use in differential air pressure (DAP) systems including data collection and utilization for general fitness use, athletic use, or medical use treadmills and related software, control and analytics systems, especially as related to obtaining gait data from load cells provided in the system. Additional improvements to the control system are also disclosed.

BACKGROUND

Conventional treadmills and other cardiovascular load inducing training equipment have historically used analog interfaces for the display of information and interactivity for adjusting various control settings such as treadmill speed, incline degree, amount of unweighting, and the like during the session. As a result, conventional treadmill and exercise equipment data has mostly existed in a fitness environment. As such, the user data collected lacks the necessary privacy and security, communication and payment management features required by the medical industry. To date, utilization of cloud connected exercise equipment has been almost non-existent in medical facilities due to privacy and confidentiality challenges to protected health information (PHI) required by the Health Insurance Portability and Accountability Act (HIPAA) and the Health Information Technology for Economic and Clinical Health (HITECH) Act. HIPAA and HITECH define PHI as individually identifiable health information including demographic information such as date of birth and zip code, that: (A) is created or received by a health care provider, health plan, public health authority, employer, life insurer, school or university, or health care clearinghouse; and (B) relates to the past, present, or future physical or mental health or condition of any individual, the provision of health care to an individual, or the past, present, or future payment for the provision of health care to an individual.

Differential Air Pressure (DAP) partial unweighting systems have typically been designed for Physical Therapists for direct use with their patients. Such systems typically contain a treadmill, a flexible bag that applies air pressure to the lower portion of the user's body, and large, continuous, unobstructed windows in the bag, that allow a therapist to observe a patient's gait mechanics in order to provide feedback and to assess issues or progress.

Expanding into markets beyond the specialized requirements of PTs, the need exists for different system capabilities as well as improved data collection modes and methods.

Differential Air Pressure (DAP) partial unweighting systems have typically comprised an OEM treadmill enclosed in a flexible bag that applies air pressure to the lower portion of the user's body. Mechanical unweighting systems have also been described. While these systems have included load cells previously for calibration prior to session start, there remains a need for improvements in load cell use during active unweighting sessions. Load cells are commonly placed under the treadmill to measure user weight for calibration, and to gauge footfalls during gait measurement.

While the present systems are effective in delivering basic unweighing therapy, the need exists for improved quality, variety and collection of unweighting session data including data collected from load cells. Still further improvements are needed for unweighting systems to be easier to maintain, and easier for users to access as well as equipped to meet the requirements of privacy and confidentiality required for patient medical records, including the data and patient electronic health records created, generated, updated before, during or after performing unweighting therapy.

SUMMARY OF THE DISCLOSURE

In general, in one embodiment, a method of calibrating an unweighting system for a user includes: (1) coupling a user to an unweighting system; (2) unweighting the user using the unweighting system to an initial unweighting condition; (3) obtaining electronic signals from a first load cell and a second load cell for the user at the initial unweighting condition; (4) increasing the amount of unweighting of the user to a first unweighting level above the initial unweighting condition; (5) obtaining electronic signals from the first load cell and the second load cell for the user at the first unweighting level above the initial unweighting condition; (6) increasing the amount of unweighting of the user to a second unweighting level above the initial unweighting condition; (7) obtaining electronic signals from the first load cell and the second load cell for the user at the second unweighting level above the initial unweighting condition; (8) increasing the amount of unweighting of the user to a third unweighting level above the initial unweighting condition; (9) obtaining electronic signals from the first load cell and the second load cell for the user at the third unweighting level above the initial unweighting condition; and (10) generating a user specific calibration curve for unweighting the user based on the electronic signals from the first load cell and the second load cell for the user at the initial unweighting condition and including the first, the second, and the third unweighting levels above the initial unweighting condition.

This and other embodiments can include one or more of the following features. The method can further include controlling operation of the unweighting system during an unweighting session for the user. The operation of the unweighting system can be controlled based on the generated user specific calibration curve. A weight of the user obtained during the initial unweighting condition can be within 10 pounds of a user weight measurement taken outside of the unweighting system. A weight of the user obtained during the initial unweighting condition can be within 5 pounds of a user weight measurement taken outside of the unweighting system. A weight of the user obtained during the initial unweighting condition can be within 1 pound of a user weight measurement taken outside of the unweighting system. The difference between the level of unweighting in the initial unweighting condition and the first unweighting level, the second unweighting level, and the third unweighting level can be a uniform change in unweighting amount between each level. The method can further include performing additional steps of increasing the amount of unweighting of the user to an additional unweighting level above the initial unweighting condition and obtaining electronic signals from the first load cell and the second load cell for the user at each of the additional steps of increasing the amount of unweighting until the amount of unweighting of the user reaching an unweighting level of 50% unweighting of the user before the generating step. The method can further include performing additional steps of increasing the amount of unweighting of the user to an additional unweighting level above the initial unweighting condition and obtaining electronic signals from the first load cell and the second load cell for the user at each of the additional steps of increasing the amount of unweighting until the amount of unweighting of the user reaches an unweighting level of 40% unweighting of the user before the generating step. The method can further include performing additional steps of increasing the amount of unweighting of the user to an additional unweighting level above the initial unweighting condition and obtaining electronic signals from the first load cell and the second load cell for the user at each of the additional steps of increasing the amount of unweighting until the amount of unweighting of the user reaching an unweighting level of 30% unweighting of the user before the generating step. The method can further include performing additional steps of increasing the amount of unweighting of the user to an additional unweighting level above the initial unweighting condition and obtaining electronic signals from the first load cell and the second load cell for the user at each of the additional steps of increasing the amount of unweighting until the amount of unweighting of the user reaching an unweighting level of 25% unweighting of the user before the generating step. The unweighting system can be a differential air pressure system or a mechanical unweighting system. The unweighting system can be a differential air pressure system and the initial unweighting condition is obtained when the differential air pressure chamber is inflated completely. The unweighting system can be a differential air pressure system and the initial unweighting condition can be provided by inflating a differential air pressure chamber to a pressure of 60 mm water. The step of generating a user specific calibration curve for unweighting the user can be based on a piecewise linear operation of the unweighting levels and the obtained load cell signals. The uniform level of change can occur in increments of 10, 15, or 20 mm H2O.

The method can further include performing the method steps by including obtaining electronic signals from a third load cell and a fourth load cell.

In general, in one embodiment, a method of calibrating a differential air pressure unweighting system for a user includes: (1) coupling a user to a chamber of the differential air pressure system; (2) increasing the pressure in the chamber to an initial unweighting condition; (3) obtaining electronic signals from a first load cell and a second load cell of the differential air pressure unweighting system for the user at the initial unweighting condition; (4) increasing the pressure in the chamber in successive increments to unweight the user to a plurality of unweighting levels; (5) obtaining electronic signals from the first load cell and the second load cell for the user at each successive unweighting increment level of the plurality of unweighting levels; (6) generating a user specific differential air pressure calibration curve for unweighting the user based on the electronic signals obtained at the initial unweighting condition and each of the successive unweighting increments; and (7) operating the differential air pressure system to unweight the user using the user specific differential air pressure calibration curve.

This and other embodiment can include one or more of the following features. The last of the unweighting levels used in generating the user specific differential air pressure calibration curve can be collected at a 50% unweighting level. The last of the unweighting levels used in generating the user specific differential air pressure calibration curve can be collected at a 40% unweighting level. The last of the unweighting levels used in generating the user specific differential air pressure calibration curve can be collected at a 30% unweighting level. The difference in unweighting level between each one of the successive unweighting levels can be 1% unweighting. The difference in unweighting level between each one of the successive unweighting levels can be 0.5% unweighting. The difference in unweighting level between each one of the successive unweighting levels can be 0.1% unweighting. The difference in unweighting level between each one of the successive unweighting levels can be 0.01% unweighting. The initial unweighting condition can be obtained when the differential air pressure chamber is inflated completely. The initial unweighting condition can be provided by inflating the differential air pressure chamber to a pressure of 60 mm water. The step of generating a user specific calibration curve for unweighting the user can be based on a piecewise linear operation of the unweighting levels and the obtained load cell signals. The successive increments can be one of 5, 10, 15, 20, 25, 30, 35 or 40 mm H2O. The method, the steps of obtaining load cell signals, can further include obtaining a signal from a first load cell positioned in a right rear portion of the differential air pressure chamber and obtaining a signal from a second load cell positioned in a left rear portion of the differential air pressure system. The method, the step of obtaining load cell signals, can further include obtaining a signal from a third load cell positioned in a right front portion of the differential air pressure chamber and obtaining a signal from a fourth load cell positioned in a left front portion of the differential air pressure system. The method, the steps of obtaining load cell signals, can further include obtaining a signal from a first load cell positioned on a right side of a strike plate under a moving portion of a treadmill within the differential air pressure system and obtaining a signal from a second load cell positioned on a left side of a strike plate under a moving portion of a treadmill within the differential air pressure system. The method, the step of obtaining load cell signals, can further include obtaining a signal from a third load cell positioned on a right side of a strike plate under a moving portion of a treadmill within the differential air pressure system and obtaining a signal from a fourth load cell positioned on a left side of a strike plate under a moving portion of a treadmill within the differential air pressure system. The method, the steps of obtaining load cell signals, can further include obtaining a signal from a first load cell positioned adjacent to a right side of a moving portion of a slat belt treadmill within the differential air pressure system and obtaining a signal from a second load cell positioned adjacent to a left side of a moving portion of a slat belt treadmill within the differential air pressure system. Two DAP load cells or four DAP load cells can be positioned relative to a treadmill within the DAP chamber. The treadmill can be a slat treadmill.

In general, in one embodiment, a method of providing gait parameters of a user during use of an unweighting system include: (1) obtaining load cell data from a first load cell and a second load cell each measuring a user interaction with a moving portion of a treadmill within the unweighting system; (2) determining when the user is impacting a right side or a left side of the moving portion of the treadmill by analyzing the load cell data from the obtaining step; and (3) identifying right side step time and left side step times from the determining step.

This and other embodiments can include one or more of the following features. The method can further include determining a user cadence in steps per minute based on the integration of load cell data from the right side step time and the left side step time. The method can further include determining a user stride length. The method can further include determining a user weight bearing symmetry. The method can further include determining a user stance time. The method can further include determining a walk-run transition for a user based on the analysis of outputs of the first and the second load cells having values greater than zero to outputs of the first and second load cells having zero values. The method can further include adapting the unweighting control of the unweighting system to a running mode after detecting the walk run transition. The differential air pressure system operation can be adjusted or processing of DAP load cell signals is modified when a transition to running mode is detected. The method can further include providing one or more DAP gait parameters after performing a stride validation method. The stride validation method can include at least three successive strides consistent with a gait analysis mode. The three successive strides can be left-right-left or right-left-right. The gait analysis mode can be a DAP walking gait analysis mode or a DAP running gait analysis mode. The stride validation method can be performed for a DAP walking gait analysis mode or a DAP running gait analysis mode.

In general, in one embodiment, a method of providing a user specific calibrated differential air pressure exercise session includes: (1) sealing a user within a chamber of a differential air pressure system; (2) inflating the chamber; (3) increasing the speed of the moving belt of a treadmill in the chamber such that the user is walking within the chamber while the user is being unweighted by air pressure in the chamber; (4) collecting data from a first load cell and a second load cell in differential air pressure system; (5) providing a user specific unweighting calibration based on the collected data; and (6) operating the differential air pressure system to unweight the user according to the user specific unweighting calibration.

In general, in one embodiment, a system for controlling a differential air pressure unweighting system includes a chamber, a pressure source in communication with the chamber; an exercise device inside the chamber; a user seal allowing a user to stand in the chamber and interact with the exercise device while maintaining an unweighting pressure in the chamber; at least two load cells positioned to obtain gait related signals from the user while the DAP chamber is unweighting the user; and a computer controller in communication with the pressure source, the at least two load cells having computer readable instructions for adjusting the unweighting level experienced by the user.

This and other embodiments can include one or more of the following features. The system can further include a third and a fourth DAP load cell. The exercise device can be a treadmill. The treadmill is a slat treadmill. The system can further include a display within view of the user while the user is sealed to the DAP chamber. The computer controller can include computer readable instructions for providing on the display one or more gait parameters obtained from the DAP load cells. The computer readable controller can include computer readable instructions for performing a stride validation before displaying one or more gait parameters to the user. The computer readable instructions can be adapted to perform any of the DAP methods described herein.

In general, in one embodiment, a system for controlling an unweighting system includes an unweighting platform, a mechanical unweighting device coupled to the platform, an exercise device coupled to the platform, a user engagement device allowing a user to stand on the unweighting platform and interact with the exercise device while maintaining an unweighting level from the mechanical unweighting device, at least two load cells positioned to obtain gait related signals from the user while the mechanical unweighting device is unweighting the user; and a computer controller in communication with the mechanical unweighting device, the at least two load cells having computer readable instructions for adjusting the unweighting level experienced by the user.

This and other embodiments can include one or more of the following features. The system can further include a third and a fourth unweighting load cell. The exercise device can be a treadmill. The treadmill can be a slat treadmill. The system can further include a display within view of the user while the user is coupled to the mechanical unweighting device. The computer controller can include computer readable instructions for providing on the display one or more gait parameters obtained from the unweighting load cells. The computer readable controller can include computer readable instructions for performing a stride validation before displaying one or more gait parameters to the user. The computer readable instructions can be adapted to perform any of the unweighting methods herein modified for implementation and performance of a user unweighted using a mechanical unweighting system.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 5A illustrates the application of a stride validation process that identifies strides that are valid when a walking mode is selected as indicated by the left side shaded area. FIG. 5B illustrates the application of a stride validation process that identifies strides that are valid when a running mode is selected as indicated by the right side shaded area. In each of these traces only the shaded strides are considered in a correct for further gait analysis.

FIG. 10A is a perspective view of a user within a DAP chamber undergoing unweighted training. The DAP chamber bag is removed to show the interior. The user is wearing a number of markers or instrumented garments with data that is detected, recorded and synthesized by the unweighting system. There are two load cells shown underneath the treadmill frame within the DAP chamber base. Two other load cells on the opposite side are present but not visible in this view. The display associated with the unweighting system illustrates a gait parameter output or recommendation obtained using one, both or various combinations of the user worn markers, garments or other data along with the load cell data collected by the unweighting system.

FIG. 13 is a flow chart of a method of an unweighting system calibration.

FIG. 14 is a flow chart of a method of an unweighting system calibration including a gain adjustment and optional maximum unweighting designation.

DETAILED DESCRIPTION

Figure 1:
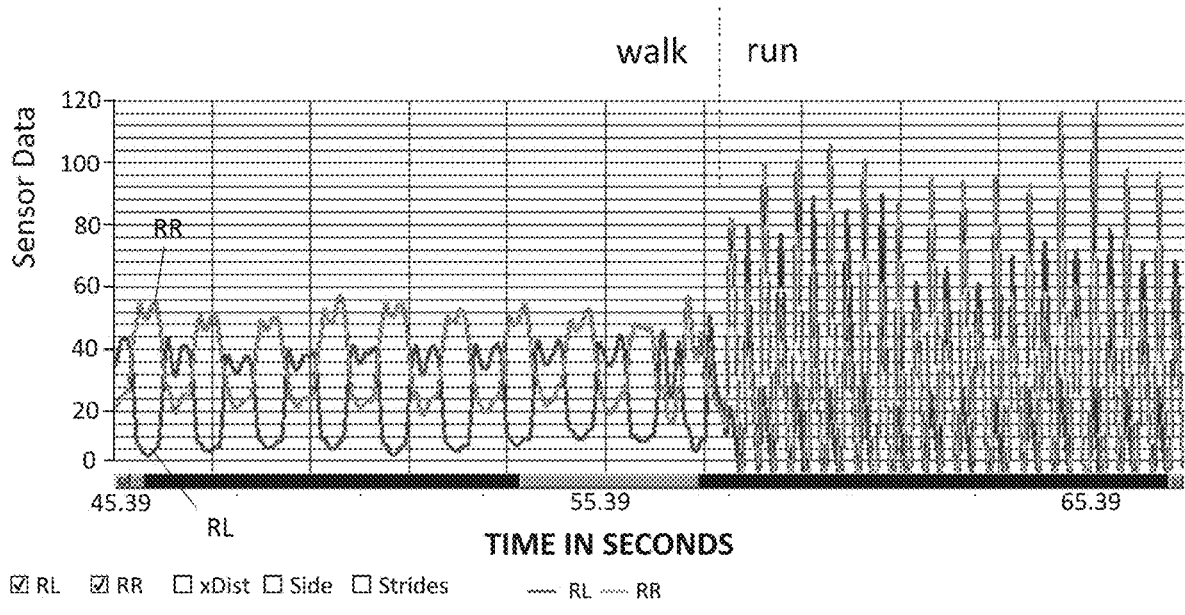
FIG. 1 is a graph of load cell sensor data collected from a right rear load cell and a left rear load cell collected over time. The signal trace shows a walking phase and a running phase of a user's gait.

Exemplary DAP systems, components and operation are illustrated and described in U.S. Pat. No. 7,591,795, U.S. Patent Application Publication No. US-2011-0098615-A1, U.S. Pat. No. 8,464,716, and U.S. Patent Application Publication No. US 2017/0128769. The commercially available AlterG P200 and M320 models are typical of existing DAP systems that are designed for physical therapists and athletic trainers. These systems comprise an exercise device, typically a treadmill, a flexible bag that applies air pressure to the lower portion of the user's body, an airtight garment which interfaces between the flexible bag and the user, and a height adjustable cockpit structure to set the height of the bag top surface to accommodate different height users.

Aspects of various embodiments of inventions described herein generally relate to systems and methods for collecting and analyzing data to aid in scheduling and managing treatment and diagnostic information provided by assisted training systems such as unweighting systems as well as other personal assistance systems. More particularly, embodiments of the invention relate to management of treatment resources and schedules such that patients in need of therapeutic treatment can access available appropriate treatments (e.g., treatments, assessments) from unweighting and assistive training systems regardless of type of treatment or location and timing of treatments. Further embodiments of this invention relate to multimodality therapy involving unweighting, personalized assistive, and various types of other forms of rehabilitation therapy, and relate to the scheduling and integration of multiple modes of therapy such as alternating time on an unweighting system to improve walking with flexibility, stretching or strength training protocols. Such multiple modes of therapy can integrate input and data captured from the unweighting therapy or assisted therapy session, patient-provided information, information from the medical records system of the therapy center, or information captured from other therapeutic rehab equipment such as bicycles, or strength testing equipment. Other embodiments of the invention relate to collecting data indicative of a user's gait using one or more load cells operated in conjunction with the unweighting system. Alternative embodiments may further involve selecting or adapting treatment based on the gait measurements including altering gait analysis protocols employed by the control system based on whether a user in the unweighting system is walking or running. Still further embodiments of the invention comprise collecting data and analyzing the data to determine whether the user has any balance or concussive impairment. Still further, there are additional improvements to the use of unweighting system load cell data to provide information on side to side balance, imbalance or impairment including crossover stepping, stride symmetry, stride validation and other similar comparison functions to further characterize the gait of the unweighting system user.

In some embodiments the gait assessment is based on data collected from one or more load cells associated with the system. Load cells may be used in conjunction with unweighting systems (whether differential air pressure or mechanical unweighting type) in any of a number of different configurations. One exemplary configuration is when four load cells are placed under a treadmill with one load cell at or near the four corners of the treadmill. Another exemplary configuration is to place load cells within the treadmill. The load cells may be positioned inside and under a slat type treadmill or inside and under a belt type treadmill. The treadmills may be of standard configuration used with a strike plate placed under the treadmill belt. In some configurations, the load cell may have a specific design such as a low profile for reduced step height as described in U.S. Patent Application Publication No. 2017/0128769. An exemplary low profile load cell is illustrated and described in relation to FIGS. 8, 13, 14A, 14B and 14C in the '8769 application.

There are available various unweighting systems suited to training users or patients in different categories based on a number of factors such as, for example, patient ability to access the machine, the specific training needs of the patient and the physical capabilities of the patient as well as whether the patient requires assistance during training and if so to what degree. The systems include air pressure unweighting systems and mechanical unweighting systems.

Air pressure unweighting systems can include differential air pressure (DAP) systems and non-DAP systems. A number of differential air pressure systems for various levels of patient assistance before, during or after use are described in the non-provisional patent application entitled "Differential Air Pressure Systems and Methods of Using and Calibrating Such Systems for Mobility Impaired Users" application Ser. No. 13/423,124 filed on Mar. 16, 2012 ("the '124 application") and U.S. Provisional Application No. 62/049,307, filed Sep. 11, 2014, titled "Unweighted Training Systems and Methods of Using and Calibrating Such Systems for Mobility Impaired or Obese Users" ("the '307 application"). The entireties of these applications are incorporated herein by reference.

Other air pressure unweighting systems are described at U.S. Provisional Application No. 62/013,999, filed Jun. 18, 2014, titled "Differential Air Pressure Treadmill System" and U.S. Provisional Application No. 62/024,916, filed Jul. 15, 2014, titled "Pressure Chamber and Lift for Differential Air Pressure System", the disclosures of which are incorporated herein by reference in their entireties.

Mechanical unweighting systems can include curved arch unweighting systems, unweighting arch systems, and cantilevered systems, among others, and are described at "SUPPORT FRAME AND RELATED UNWEIGHTING SYSTEM," filed Mar. 14, 2013, application No. 61/784,387; "CURVED ARCH UNWEIGHTING SYSTEMS," application No. 61/772,964, filed Mar. 5, 2013; "UNWEIGHTING ARCH SYSTEMS," application No. 61/773,019, filed Mar. 5, 2013; "MONOCOLUMN UNWEIGHTING SYSTEMS," application No. 61/773,037, filed Mar. 5, 2013; and "CANTILEVERED UNWEIGHTING SYSTEMS," filed Mar. 14, 2013, application No. 61/784,510, each of which is incorporated by reference in its entirety.

In addition, this application may be related to operation of any of the unweighting systems or auxiliary systems or patient interface embodiments described in any of the following patent applications, each of which is herein incorporated by reference in its entirety: U.S. Provisional Application No. 61/785,402 filed on Mar. 14, 2013; International Application No. PCT/US2014/028032 filed on Mar. 14, 2014. U.S. Pat. No. 7,591,795 issued on Sep. 22, 2009; U.S. application Ser. No. 12/236,459 filed on Sep. 23, 2008; U.S. application Ser. No. 12/236,465 filed on Sep. 23, 2008; U.S. application Ser. No. 12/236,468 filed on Sep. 23, 2008; International Application No. PCT/US2006/038591 filed on Sep. 28, 2006; U.S. Provisional Application No. 60/999,102 filed on Oct. 15, 2007; U.S. Provisional Application No. 60/999,101 filed on Oct. 15, 2007; U.S. Provisional Application No. 60/999,061 filed on Oct. 15, 2007; U.S. Provisional Application No. 60/999,060 filed on Oct. 15, 2007; U.S. application Ser. No. 12/761,316 filed on Apr. 15, 2010; U.S. application Ser. No. 12/761,312 filed on Apr. 15, 2010; International Application No. PCT/US2008/011832 filed on Oct. 15, 2008; International Application No. PCT/US2008/011807 filed on Oct. 15, 2008; U.S. Provisional Application No. 61/178,901 filed on May 15, 2009; U.S. application Ser. No. 12/778,747 filed on May 12, 2010; International Application No. PCT/US2010/034518 filed on May 12, 2010; U.S. Design Application No. 29/337,097 filed on May 14, 2009; U.S. Provisional Application No. 61/454,432 filed on Mar. 18, 2011; U.S. application Ser. No. 13/423,124 filed on Mar. 16, 2012; International Application No. PCT/US12/29554 filed on Mar. 16, 2012; U.S. Pat. No. 5,133,339 issued on Jul. 28, 1992; U.S. Provisional Application No. 61/651,415 filed on May 24, 2012; U.S. Provisional Application No. 61/785,317 filed on Mar. 14, 2013, titled "METHOD OF GAIT EVALUATION AND TRAINING WITH DIFFERENTIAL PRESSURE SYSTEM"; International Application No. PCT/US2014/029578 filed on Mar. 14, 2014; U.S. Patent Application Publication No. 2016/00007885; U.S.

Provisional Application No. 61/784,387 filed on Mar. 14, 2013, titled "SUPPORT FRAME AND RELATED UNWEIGHTING SYSTEM"; International Application No. PCT/US2014/029002 filed on Mar. 14, 2014; U.S. Provisional Application No. 61/772,964 filed on Mar. 5, 2013; International Application No. PCT/US2014/020741 filed on Mar. 5, 2014; U.S. Provisional Application No. 61/773,019 filed on Mar. 5, 2013; U.S. Provisional Application No. 61/773,037 filed on Mar. 5, 2013; International Application No. PCT/US2014/020863 filed Mar. 5, 2014; U.S. Provisional Application No. 61/773,048 filed on Mar. 5, 2013; International Application No. PCT/US2014/020934 filed on Mar. 5, 2014; U.S. Provisional Application No. 61/784,664 filed on Mar. 14, 2013 titled "UNWEIGHTING GARMENTS"; U.S. Provisional Application No. 61/784,510 filed on Mar. 14, 2013, titled "CANTILEVERED UNWEIGHTING SYSTEMS"; International Application No. PCT/US2014/028694 filed on Mar. 14, 2014; U.S. Provisional Application No. 62/049,307 filed on Sep. 11, 2014, titled "UNWEIGHTED TRAINING SYSTEMS AND METHODS OF USING AND CALIBRATING SUCH SYSTEMS FOR MOBILITY IMPAIRED OR OBESE USERS"; U.S. Provisional Application No. 62/013,999 filed on Jun. 18, 2014, titled "DIFFERENTIAL AIR PRESSURE TREADMILL SYSTEM"; U.S. Provisional Application No. 62/042,916 filed pm Jul. 15, 2014, titled "PRESSURE CHAMBER AND LIFT FOR DIFFERENTIAL AIR PRESSURE SYSTEM"; U.S. Provisional Application No. 62/049,149 filed on Sep. 11, 2014, titled "UNWEIGHTING GARMENTS", each of which are incorporated by reference its entirety.

The various load cell embodiments and configurations can include one or more of the following features. In one aspect, the base of an unweighing system can further include a low profile configuration of a load cell and a gait measurement device coupled to the treadmill base and in position relative to the treadmill deck. In another aspect, the base can further include a low profile configuration of a load cell coupled to the treadmill base and in position relative to the treadmill deck. In a further aspect, the base can further include a front pair of low profile measurement devices and a rear pair of low profile measurement devices coupled to the treadmill base and in position relative to the treadmill deck. In an alternative aspect, the measurement devices can be one or more of a cushioning element, a measurement device, a load cell, a gait measurement device, a dampening device or a sensor. In yet another aspect, the base can further include at least one low profile configuration load cell including: a load cell coupled to a portion of the treadmill base; a damper attached to the load cell; and a treadmill deck mount connected to a bottom surface of the treadmill deck and to the damper. In still another aspect, the damper can be made from rubber or a shock absorbing material. In other load cell configurations, there may be only a pair of load cells coupled to the left right and the left rear of the unweighting system. As described herein, one or more load cells may be coupled to a strike plate or impact plate or sensor under a moving platform of a treadmill. Optionally, one or more load cells may be coupled to the unweighting chamber underneath a treadmill. In still another configuration, one or more load cells are coupled to rollers, rails or support underneath a moving platform of a treadmill. Each of the above alternative configurations may be utilized in belt or slat style treadmill moving surfaces.

This and other embodiments can include one or more of the following features. In one aspect, the damper can be replaced with aluminum, a metal or a hard non- or low-shock absorbing material. In another aspect, the treadmill deck top can be about the same height from the treadmill base as an uppermost portion of a treadmill deck frame to damper attachment point. In a further aspect, the base can further include a front pair of low profile cushioned load cells and a rear pair of low profile hard or non-cushioned load cells. In an alternative aspect, the load cell and damper configuration can be adapted and configured to improve load cell signal to noise output. In yet another aspect, the load cell and damper configuration can be adapted and configured to specifically improve load cell signal to noise output for a gait measurement device or process used in conjunction with a therapy performed using a system having the base. In still another aspect, the base can further include an airtight, externally accessible tracking angle adjustment component positioned for adjustment for one or both of the front roller or the rear roller.

As described in the embodiments that follow, there is provided an explanation of the system configurations and the algorithms employed in an improved software application to measure gait parameters such as cadence, weight-bearing symmetry, stance times and lengths using load cells associated with an unweighting system such as a mechanical unweighting system or a differential air pressure system. One exemplary implementation of the software is in the M320 Stride Smart software application developed by AlterG, Inc. In one aspect, there is provided separate gait processing algorithms are employed for walking versus running. In one aspect, the software system may analyze user stride, cadence or other gait parameter and determine whether the user is walking or running and conduction data collection and analysis based on that determination. In still other aspects, the user selects the mode of gait analysis (running or walking) from a touch screen, a push button or other suitable indicator operable by the user or an assistant during unweighting therapy.

In one particular aspect, the gait performance characteristics are obtain by analyzing weight distribution and force peaks from the load cells associated with the unweighting system treadmill. In some embodiments, the improved method provides a signal that tracks right side movement versus left. The side trace is the key to stride time measurement and weight-bearing symmetry. Combining high-speed digital video review, embodiments of the Stride Smart software system provide enhanced data collection and assessment tools for evaluating gait and improving performance in a wide array of unweighting systems. In some aspects, the gait software system obtains and performs gait data collection and analysis by taking advantage of the variance in weight distribution between left side and right side load cells during unweighted training.

In general, three approaches are conventionally used to measure gait performance: Pressure Mat; Video and Force Plate.

A pressure mat is a surface instrumented with many small pressure sensors. It measures the pressures applied by the foot in a gait stride. The forces measured in each pressure cell can be rendered as an image and further processed to derive gait measurements. Alternatively, flexible mats can be inserted into shoes and pressures measured from stride-to-stride.

Figure 3:
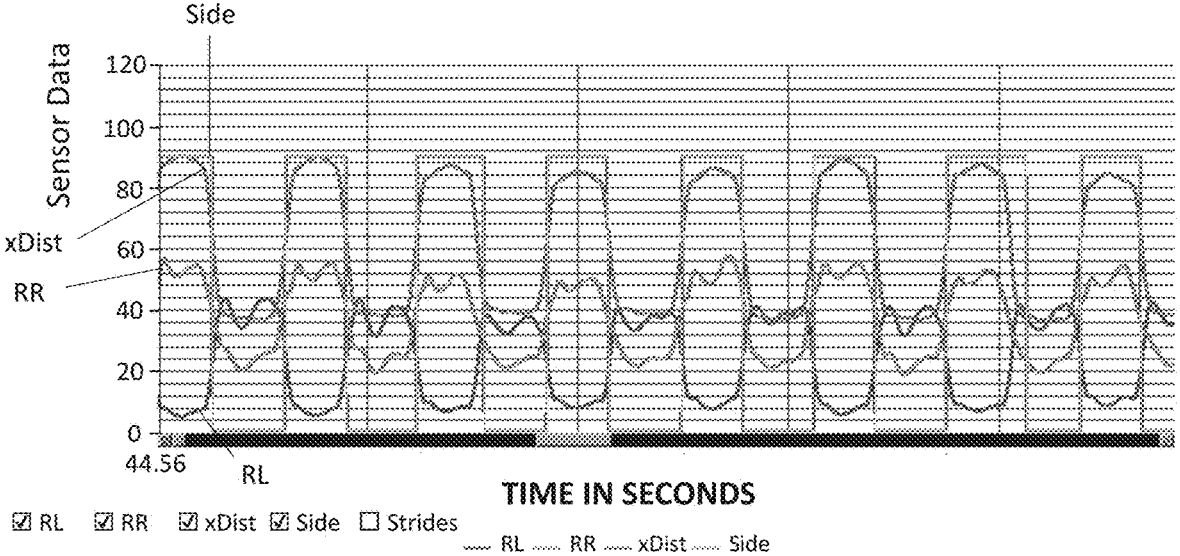
FIG. 3 is a graph of load cell sensor data collected from a right rear load cell and a left rear load cell collected over time from the walking phase of FIG. 2 with the addition of a square wave side trace added over the x-distribution curve to more clearly delineate the user's left-right weight transitions.

Video techniques record sequential images of the subject to analyze range of motion of key joints. Video analysis systems rely on affixed anatomical markers to the user at key joints as is illustrated and described in the context of unweighting systems in US Patent Application Publication US 2016/0007885, see FIGS. 3 and 8. Software tracks the motion of the joints and reports measurements related to joint range-of-motion, velocity and acceleration.

A force plate is a platform instrumented with load cells in the four corners. The platform is designed to distribute weight evenly over the surface of the top plate. Each load cell measures the force applied at its location and the four contributions summed to yield total weight. The position of load cells within an unweighting system is similar to that of the force plate namely in four corners in relation to the treadmill or in a load cell pair in a rear position.

Many unweighting systems currently employ load cells associated with the treadmills to conduct preliminary calibration of the unweighting system. Embodiments of the gait collection and analysis system described herein take advantage of some existing unweighting system components to enable gait measurements as it allows the subject to ambulate continuously without any connecting wires. As described herein, there are also provided digital cameras on, in or within the unweighting system that are used to collect and store high-speed videos for review, including collection of video and gait data in a common data and time stream ensuring synchronization of the various data streams. In still further embodiments, the use of high-resolution data acquisition from the sensors, the Stride Smart software system measures and reports the following parameters:

Cadence—Number of steps per minute
  Weight Bearing Symmetry—Ratio of weight (force-seconds) applied between right and left sides
  Step Length—Length of right or left step
  Stance Time—Amount of time spent on a side (based on balance)
Data Collection In one aspect, gait measurements are made by comparison and analysis of data from the load cells associated with the treadmill. In one aspect, gait data collection and analysis is achieved using only signals from the right-rear and left-rear load cells of the treadmill. In one embodiment, load cell data points are digitized and stored as a time-based series at a frequency of 10 Hz, 50 Hz or 100 Hz. As used herein, Hz indicates the number of samples taken per second. In the case of a sample rate of 100 Hz, this results in stance time measurements are accurate to within 10 milliseconds. In one specific example, a stance time measurement of one half second would have an accuracy of 2%.

Advantageously, in some embodiments, the unweighting system includes four load cells (front pair and rear pair). In some configurations, the unweighting system may have only one pair of rear load cells. Still further, an unweighting system may include four load cells but based on operations of the unweighting system elect to provide unweighting system gait feedback using less than all of the load cells or only two load cells or only the rear pair of load cells.

Based on testing conducted in unweighting systems, improved load cell based gait information and unweighting controls were realized using load cell algorithms focused on the rear load cells. Advantageously, the use of the rear load cells avoided noise from generated from the front load cells. It was observed that the front load cells tend to vibrate more as the subject walks or runs creating noise. Additionally, the rear load cell pair will register user information even with the treadmill is in an inclined configuration. It was observed that the front load cells do not register force when treadmill incline is used.

FIG. 1 illustrates data collected from the treadmill during walking and running phases. Note that load cell data collected while walking (left side), the signals never drop to zero meaning that the subject is always in contact with the platform. While running, right side data, the load cell signals achieve clean force peaks followed by periods of no data. Advantageously, such a load cell pattern recognition may be used to in a number of different pattern-recognition algorithms for gait analysis based on walking or running and the transitions from one to another.

Figure 2:
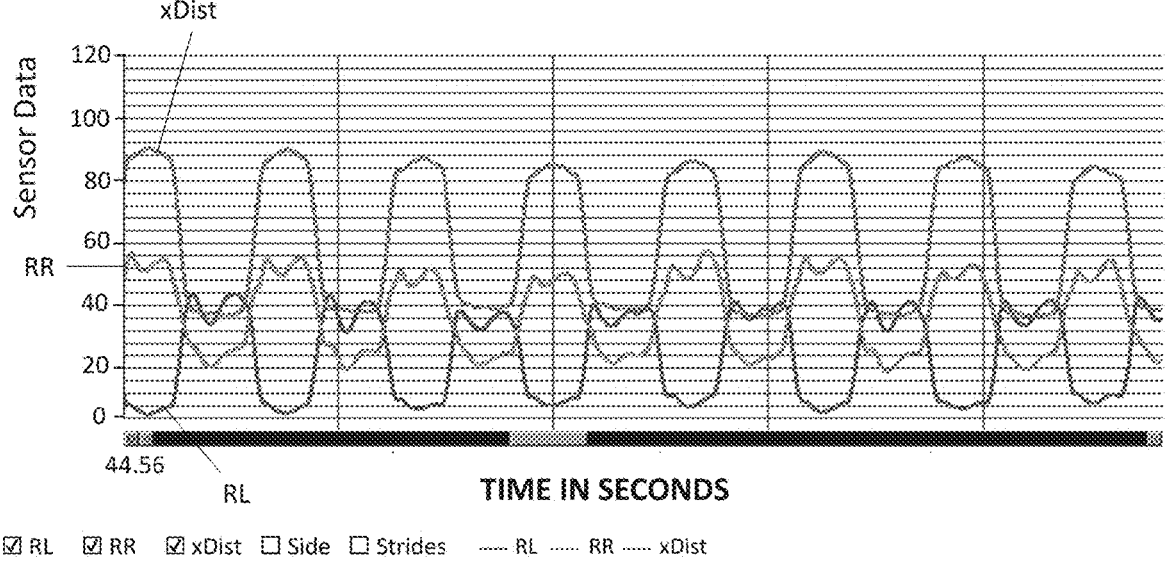
FIG. 2 is a graph of load cell sensor data collected from a right rear load cell and a left rear load cell collected over time from the walking phase of FIG. 1. The signal trace shows a walking phase and includes a trace of an x-distribution curve indicating the user's left-right weight transitions.

Additionally, it has been observed that one key to accuracy in measuring gait lies in determining when the subject is on the "right" side versus the "left" side. Once the side-to-side transition points are established, computing the gait parameters is straightforward. The challenge is to establish these points of transition within the context complicated by the operation of an unweighting system influencing the interaction between the user, the treadmill and the load cells.
Walking Data—The "X Distribution" Curve FIG. 2 is an exploded view of the walking phase of the sensor data from FIG. 1. The additional (blue) trace derives from the two load cell signals. It represents the shift in weight distribution from side to side. Using that post-processed signal, the application generates a "side change" function shown in FIG. 3.

Figure 4:
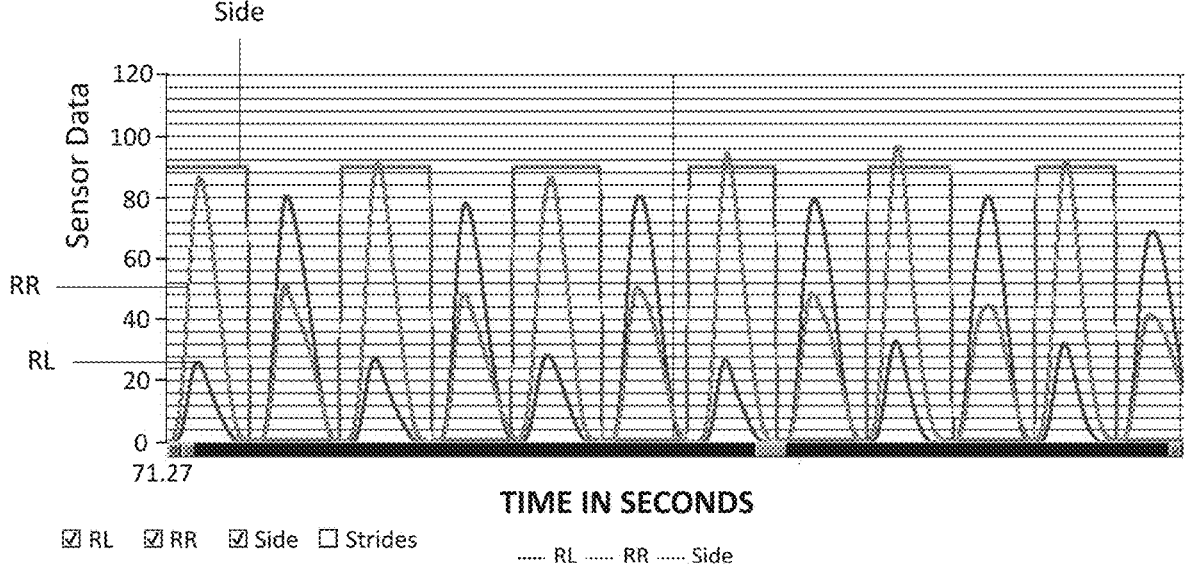
FIG. 4 is a graph of load cell sensor data collected from a right rear load cell and a left rear load cell collected over time from the running phase of FIG. 1 with the addition of a square wave side trace added to more clearly delineate the user's left-right weight transitions during the running phase.

The "side" trace identifies the points in time where the subject's weight transitions from right-to-left and back to right. The top of the side trace corresponds to the subject's right while the bottom is left. As a sanity check, note that the rear-right sensor signal (RR) peaks when the side trace is high.
Running Data—Peak Detection FIG. 4 illustrates sensor signals for running data. Side detection finds the points at which peaks occur. Note that both sensor signals "bottom out". There are times during each stride where no force is applied.
Stride Validation There are times when the walking and running algorithms will not properly identify strides. This occurs when:

Belt speed is in transition
  Subject is running when "walking mode" selected
  Subject is walking when "running mode" selected
  Subject is cross-stepping
  Confirmation checks are applied to each "detected" stride. If the confirmation check fails, the stride is marked as "invalid" and does not contribute its measurements to the reported averages. Confirmation checks compare the relative magnitudes of the sensor values and reject the stride if the values are contradictory.

Figure 5A:
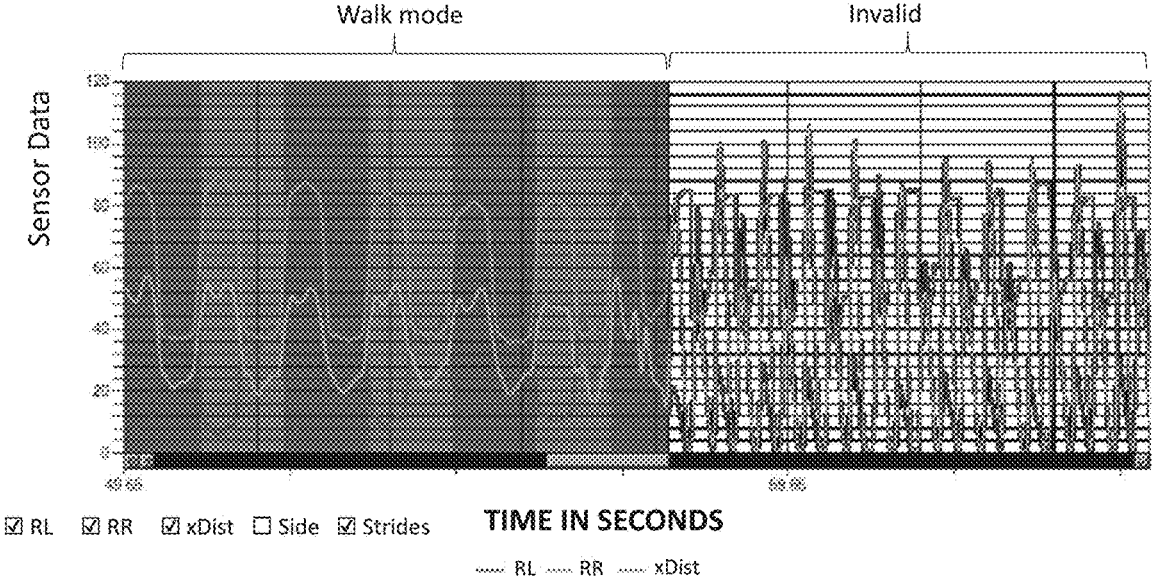
FIGS. 5A and 5B are graphs of load cell sensor data collected from a right rear load cell and a left rear load cell collected over time. The signal trace shows a walking phase and a running phase of a user's gait.
Figure 5B:
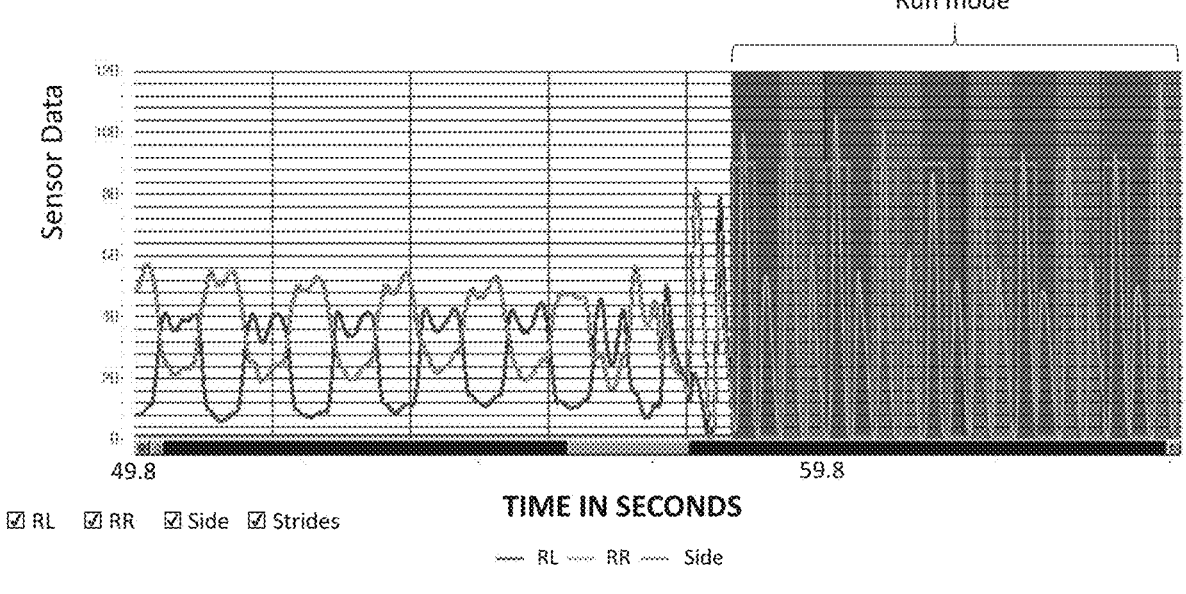
Figure 6:
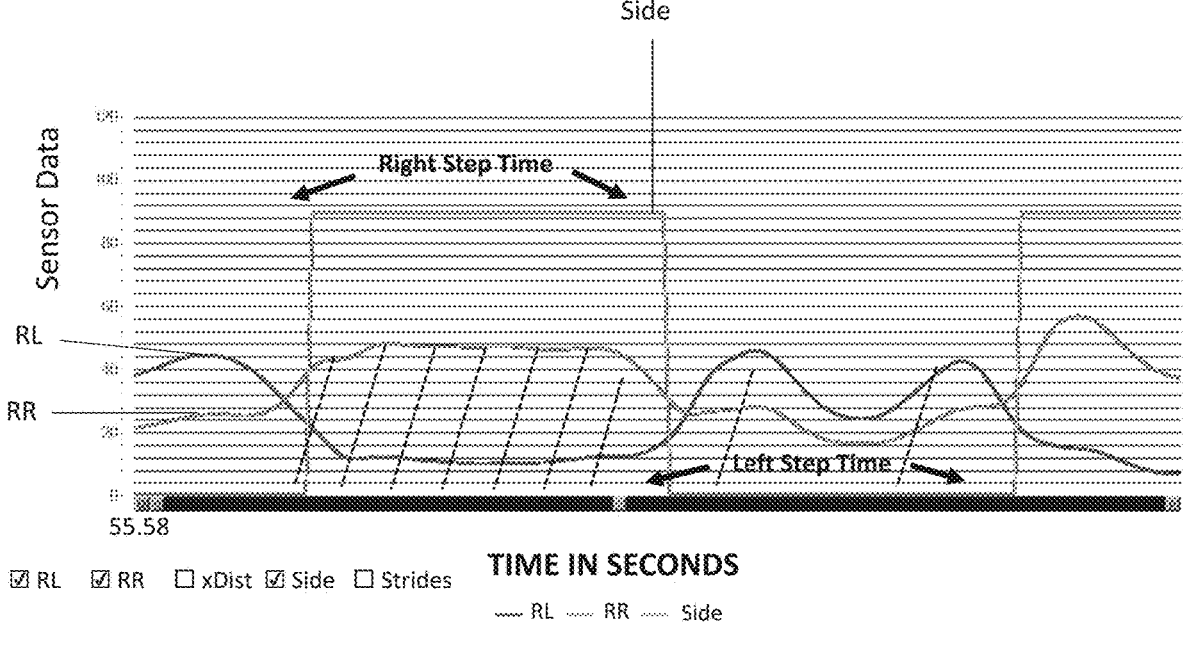
FIG. 6 is a graph of load cell sensor data collected from a right rear load cell and a left rear load cell collected over time but marked to indicate a right step time and a left step time. The trace also includes a side trace (square wave) delineating left-right transitions. Additionally, the relative amplitude and duration of the sensor signals are used to determine weight symmetry and other gait parameters.

FIGS. 5A and 5B illustrates two snapshots of walking in transition to running. Gray strip-lines highlight the strides considered "valid". In the left snapshot, FIG. 5A, "walking" mode was selected and strides considered valid for walking are highlighted. After transitioning to running and selecting the "running mode" option, the strides considered valid for running are highlighted. See FIG. 5B.
Stride Times and Symmetry FIG. 6 illustrates a single stride composed of a right step and a left step. The period of the transitions of the side trace yields right and left step times as indicated in FIG. 6. The step length is calculated from the step time and speed of the treadmill. Cadence is also derived from the stride time. Weight-bearing symmetry is calculated by integrating the area under the load cell signals on each side. The ratio of area of each side to the sum constitutes the symmetry calculation. For example, if the area on the right side is 53% of the summed areas, the symmetry is 53% right and 47% left.

In still further improvements for unweighting systems, there may also be provided new controllers and associated systems. In one exemplary embodiment, there is provided improved computer controlled system for operations and data collection of differential air pressure unweighting systems. In one aspect, there is provided an improved and consolidated electronic controller including data from or related to DAP system pressure sensors, DAP system pressure control valve, blower speed control and functions, treadmill operations and controls and a PID controller with algorithm and enhanced features. Additionally, this improvement provides for individual output signals from all load cells associated with the treadmill used with the unweighting system. In one specific embodiment, the improved electronic control is embodied in a micro/pressure control board including microprocessor control and processing capabilities. Additionally, this improved controller also provides capability for real time data streaming allowing real time or during session gait analytics during an unweighting session based on treadmill load cells. Additionally, there is also a capability to upload a raw, a processed or a portion of a data stream collected from any sensor associated with an unweighted system or unweighting session.

Improved PID Controller (Pressure/Integral/Derivative)

In one embodiment, the new micro/pressure board has a contemporary processor which allows the pressure control feedback loop to run faster as compared to previous designs. The valve positioning algorithm is also improved allowing the air valve to move more rapidly in response to the feedback controller. The net result is responsive pressure control which maintains the subject at the desired % BW as they are walking or running.

Cloud Metrics

Additionally, the above described Micro/Pressure board firmware generates a raw data stream that is captured and uploaded to an AlterG cloud database, along with Gait measurements and machine metrics. In capturing this dataset, a load cell enabled unweighting system is able to:

Provide real-time reporting through a web portal

Maintain a database of normative and pathology results

Regenerate reports based on improvements in gait algorithms

Track performance of physical hardware for service

A list of exemplary database fields captured for each session shown below:

[TimeStamp]
[UserGUID]
[UnitID]
[StartTime]
[EndTime]
[HeightInches]
[WeightLBS]
[Gender]
[DOB]
[SAEUnits]
[UserWeight]
[Distance]
[Calories]
[Cadence]
[MaxSpeed]
[AvgSpeed]
[MaxIncline]
[AvgIncline]
[MaxUnweight]
[AvgUnweight]
[MaxHeartRate]
[AvgHeartRate]
[RawData]

In still further alternative embodiments, the unweighted systems described herein may also include one or more of the following additional capabilities or expanded features:

Improved DAP calibration: Load cell based unweighting calibration is performed using load cells associated with the treadmill to collect multiple data points indicating load cell weight indication and DAP level for more than 2, more than 5, more than 10, dozens or a hundred of more DAP level/weight set points to calibrate the DAP system session for a particular user prior to conducting a DAP training session. Still further, while capturing multiple additional DAP—weight data points, the multiple pressure readings using the load cells provide a user specific DAP calibration curve for that user/session. This same DAP—weight data is also used to calculate or determine the "lowest unweighting level" for that user. In some cases, the lowest unweighting level may be only 30% or 40% of user weight.

Improved DAP control system during DAP system: Using any of the various treadmill associated load cell configurations described herein, there is also provided a DAP system control loop where DAP parameters are adjusted based on DAP load cell gait analytics to adapt the DAP session under a variety of circumstances. In one embodiment, the Stride Smart software system for Gait Feedback is used to automatically set, adjust or suggest adjustment to the DAP air pressure directly related to the quality of the human gait as measured by the DAP load cell based gait system. In still another embodiment, there is provided a DAP session model where a user or a care provider may indicate that the DAP system is to control one or more DAP system controls, such as the treadmill speed, incline alone or in combination with DAP air pressure based on the treadmill load cell collected gait feedback. In one aspect, there is provided a DAP session wherein one or more gait parameters are selected from improvement or isolated for training such as specific step length, stance symmetry, and cadence and the DAP system then adjust system parameters such that the user's performance remains within those parameters. In this way, the treadmill based load cell gait collection and analysis system may be used for more specific gait characteristic training.

It is to be appreciated that in various other alternative unweighting systems and methods, each of the above improvements may be incorporated into any of the unweighting systems, controls, methods of use, methods of data collection, methods of gait data collection and analysis and the like described herein or incorporated by reference.

Calibration

In still other aspects of the improved use of load cell data, there are provided improved unweighting system calibration algorithms employed by the unweighting system firmware. The purpose of unweighting system calibration is to determine the appropriate amount of unweighting to apply to a user in order to unweight that user by a specific desired unweighting amount. In the case of a differential air pressure chamber unweighting system, the differential air pressure bag pressure is calibrated so as to lift the subject by a specific amount of weight. The unweighting response depends on the specific configuration of the unweighting system as well as the unweighting response (whether in terms of pressure or mechanical unweighting). Still further, the unweighting response of a particular unweighting system may also depend on several factors including the fit of the shorts and the general size and shape of the user. The methods 1300 and 1400 provide additional details. (See FIG. 13 and FIG. 14).

In one embodiment, the unweighting calibration sequence is divided into four phases—inflation, initial measurement, calibration and validation. In one embodiment, the control system of the unweighting system builds a set of piece-wise linear equations. It has been observed that the use of piece wise linear fit provides an increased level of accuracy during unweighting operations. Still further, by calibrating the unweighting system to the user each time, there is increased accuracy and reliability on session to session comparisons and comparison between users since the amount of unweighting is assured by the calibrations protocols when unweighing the subject. In other embodiments, a maximum unweighting level may be provided rather than determined by the DAP system. In another embodiment, full scale of the DAP system load cells may be adjusted to increase sensitivity to a less than full scale weight range. In one aspect, a gain is applied to the DAP load cells to produce a DAP unweighting range of less than the full scale DAP unweighting range. In various embodiments, the gain applied to the DAP load cells produces an unweighting range of 0-150 lbs, 0-200 lbs, 0-300 lbs, 0-400 lbs, 0-500 lbs or 0-600 lbs. In some embodiments, a desired load cell gain level is applied to the DAP system load cells prior to performing a user specific calibration method.

It has been observed that unweighting calibration procedures using a simple linear equation to fit a subject's percent body weight to pressure may be less accurate in some ranges of unweighting. In the simple linear equation fit, two unweighting measurements were made—one at 80% body weight and a second at 20% body weight. From these two unweighting data points, a linear equation of the form "y=mx+b" was generated. Thereafter, no other load cell information was utilized and the unweighting system treated all levels of unweighting as equally achievable by the unweighting system. However, prior experience with this type of unweighting calibration method revealed a number of limitations. In some instances, the typical unweighting chamber pressure response curve is not linear. This nonlinear response of the DAP chamber led to errors at some body weights. Under this protocol, a user was to be unweighed to 20% or the calibration could not be completed. This requirement may not be met by some body types or may require an extended calibration time.

Figure 7:
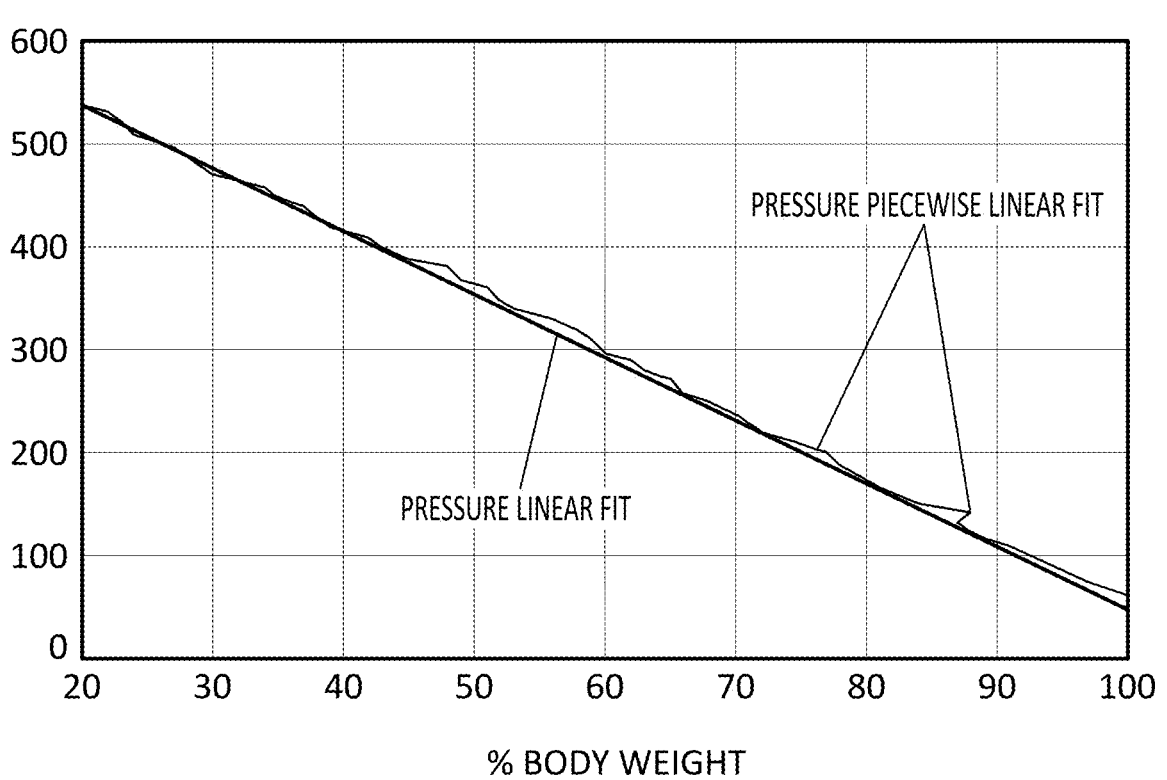
FIG. 7 is a graph illustrating the pressure response of a differential air pressure system at various levels of unweighting for a 220 lbs user. The pressure linear fit curve is a line drawn between 80% body weight (20% DAP unweighting) and 20% body weight (80% DAP unweighting). The pressure piecewise linear fit is a curve obtained by collecting dozens of data points of % body weight/% DAP unweighting and corresponding pressure response from 100% body weight to 20% body weight. The linear fit is then provided between adjacent incremental % DAP unweighting levels. Also shown are the segments of deviation between the linear fit and the piecewise linear fit.

Embodiments of an improved load cell calibration process overcome many of these shortcomings. FIG. 7 illustrates plots of various pressure and weight measurements made during a calibration process. The curve 701 was produced from 50 measurements of various levels of pressure/% body weight. The curve 701 is a plot line representing a typical pressure calibration curve for a 220-pound subject. In contrast, the curve 702 was produced using a conventional linear fit of two unweighting measurements—one made at 80% body weight and the second at 20%. The interesting thing to note is how the blue curve deviates from the orange curve at some points. It means that the linear fit does not always match the actual pressure needed to achieve a certain body weight.

Piece-Wise Linear Unweighting Calibration Model

The concept of the Piece-wise model is to make many measurements during the calibration process and linearly interpolate between the two closest data points. The advantages of this approach are:

Obtaining the pressure needed for a specific body weight is extremely accurate—the calibration locks on to deviations in the pressure response curve and tracks non-linearity.

The system does not have to unweigh the subject all the way down to 20% of body weight for calibration to be useful. For example, if the subject can only unweigh to 40% of body weight, the calibration will be accurate to that point and will restrict further unweighing. This makes the treadmill system usable for a broader range of subjects.

Calibration Phases

Phase 1: Inflates the bag to a starting pressure of 60 mm-H20

Phase 2: Measures the subject's weight at the starting pressure (also known as the "AlterG" weight)

Phase 3: Slowly increases bag pressure and makes successive weight and pressure measurements Phase 4: Gently deflates the bag and validates the measurements. Bag may deflate to starting pressure during validation.

Turning now to exemplary locations of load cells in a number of different unweighting systems.

Figure 8:
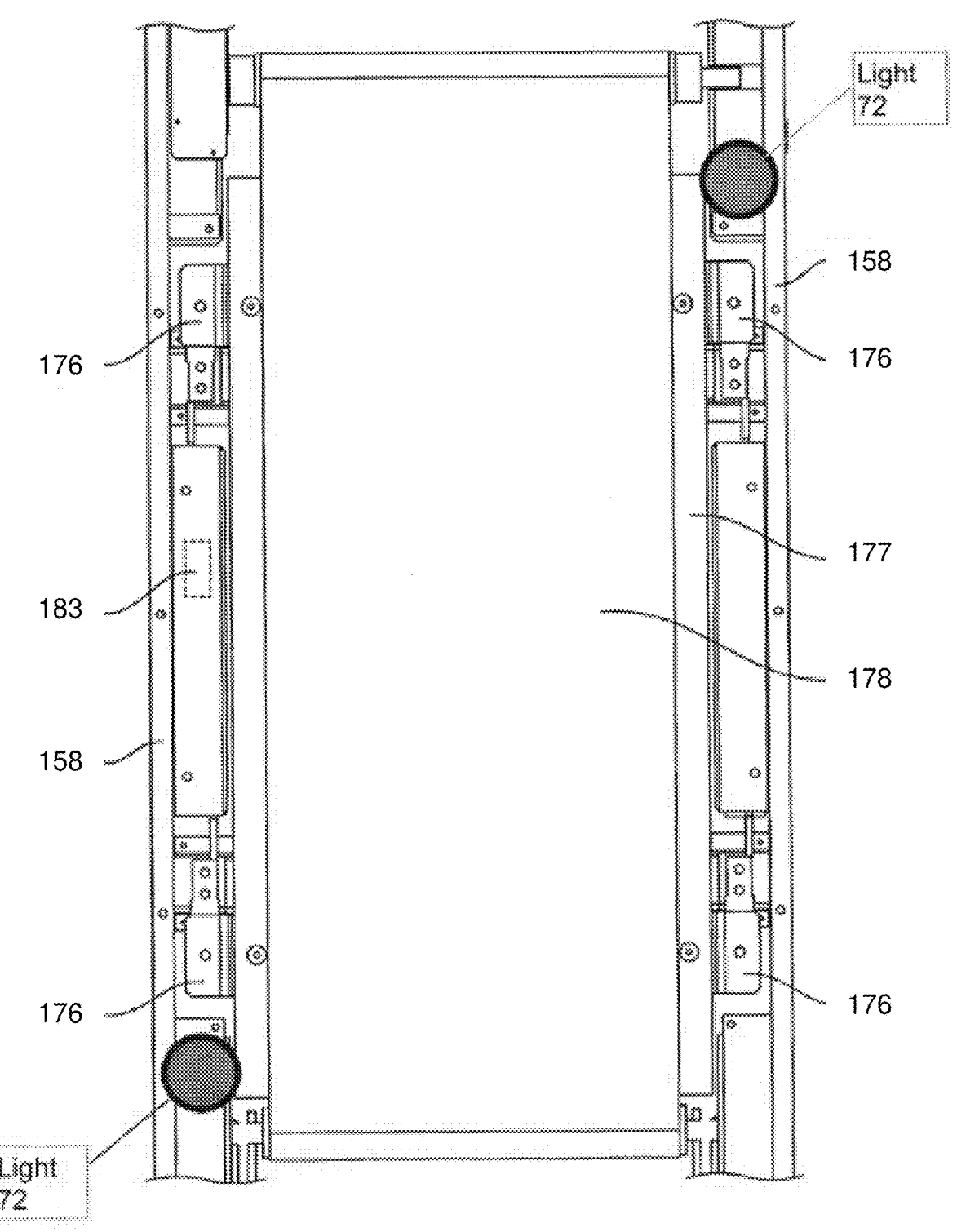
FIG. 8 is a top down view of a treadmill within a base of a differential air pressure system. The position of four load cells are shown in front right, front left, rear right and rear left positions.
Figure 9A:
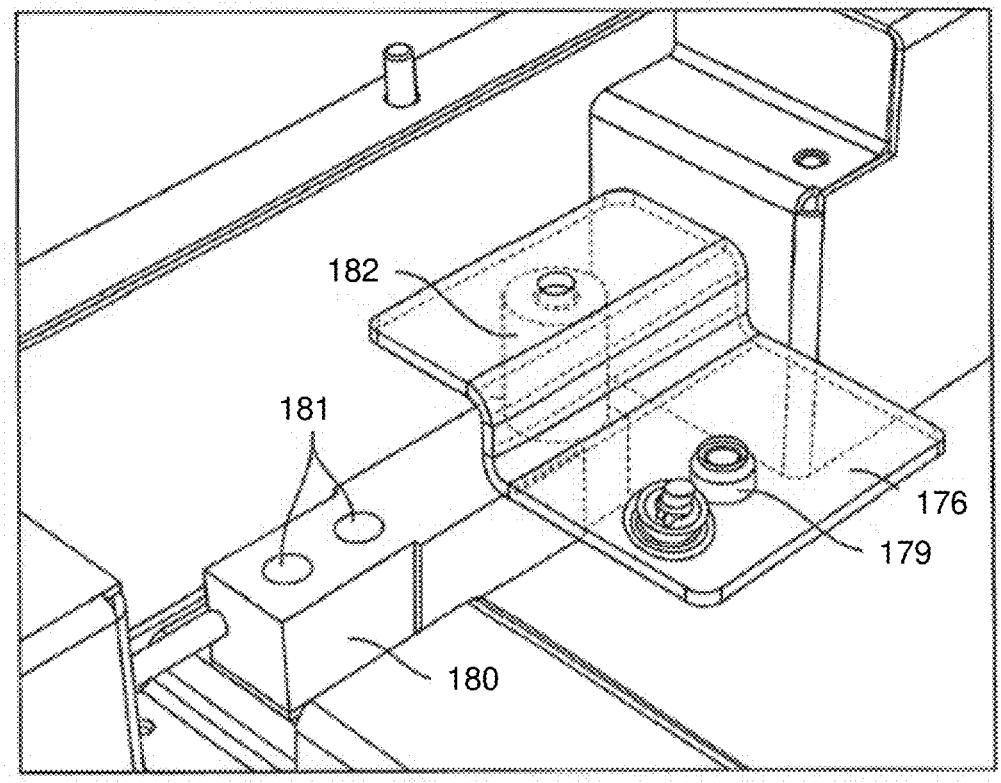
FIG. 9A is a perspective view of a load cell of FIG. 8 with a strike plate removed.
Figure 9B:
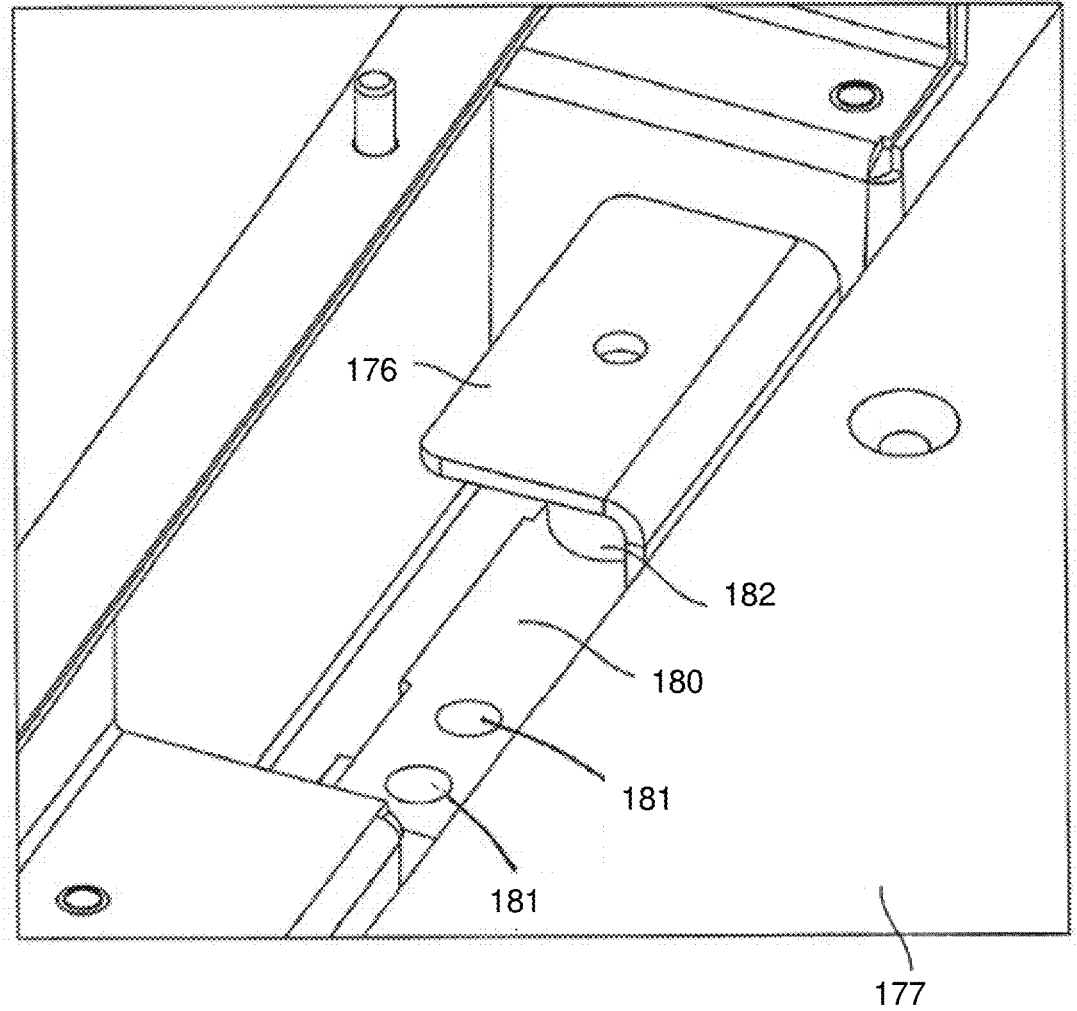
FIG. 9B is a perspective view of the load cell of FIG. 9A in relation to a strike plate.
Figure 9C:
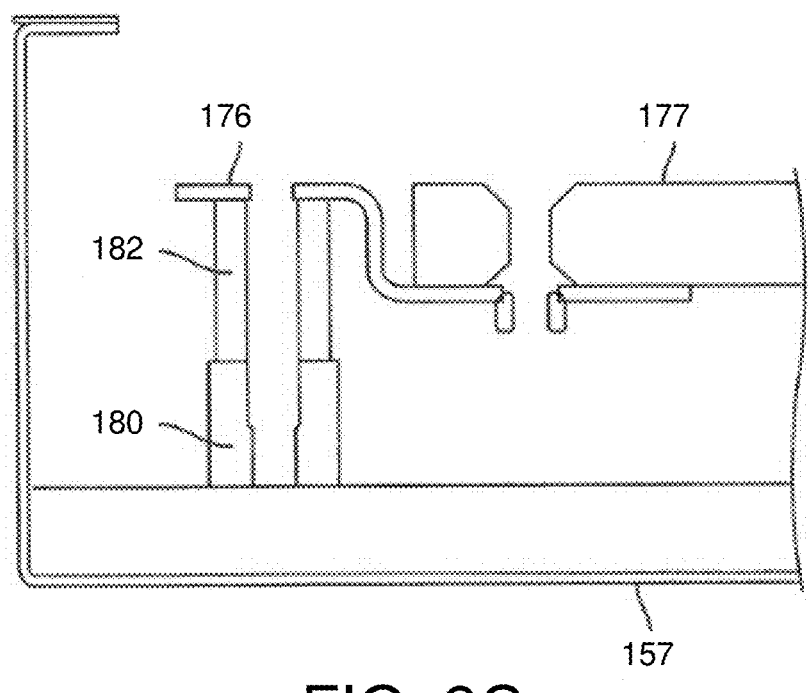
FIG. 9C is a cross section view of the load cell and strike plate of FIGS. 9A and 9B taken from the arrangement of load cells shown in FIG. 8.

FIGS. 8-9C illustrate an exemplary load cell location in relation to a strike plate under a treadmill moving platform.

FIG. 8 is a top down view between the front 168 and rear 173 rollers of a treadmill. of FIG. 8. This view shows the deck 177 below the top surface of belt 178 is suspended by deck mounts 176. This view shows the relative locations of the load cells/sensors as well as the available support areas within the pressure seal frame available for mounting other additional components or accessories within the treadmill pressure volume. Also shown is one of several possible locations for a within pressure volume treadmill deck mounted gait sensor 183 or, optionally, an appropriately configured gait metrology unit.

FIG. 9A is an enlarged perspective view of a lead cell and treadmill deck mount 180 of the treadmill base of FIG. 8 with the treadmill tread 178 removed. FIG. 9B is a perspective view similar to FIG. 9A with the treadmill deck 177 in place to illustrate the comparable height between the treadmill tread height and the overall height of a load cell 180, a damper 182 and a deck mount bracket 176. FIG. 9C is a cross section view of the mount and bracket 176 of FIG. 9B. Dimensions of the associated components may be a damper 182 with a height of about 1.6" from the top of the load cell 180 to the deck mount 176. The load cell 180 may be about 1.2" tall.

Deck mounts 176 are attached to deck 177 at attachment points 179. Deck mounts 176 are offset such that load cells 180 and dampers 182 can be mounted beside deck 177 and do not add vertical height to the overall assembly. Load cells 180 are attached to base 157 at attachment points 181. In the current embodiment, all deck mounts 176 are attached to load cells 180 through dampers 182. In an alternate embodiment that improves gait signal quality, front load cells 180 and deck mounts 176 are attached via dampers 182 as shown while rear load cells 180 and deck mounts 176 are rigidly coupled. Thereafter, only rear load cells are used during treadmill operation for gait measurements. This arrangement would also lessen sensitivity to the tolerance stack-up between base 157 and deck 177 causing variations in load cell zero readings.

Figure 10B:
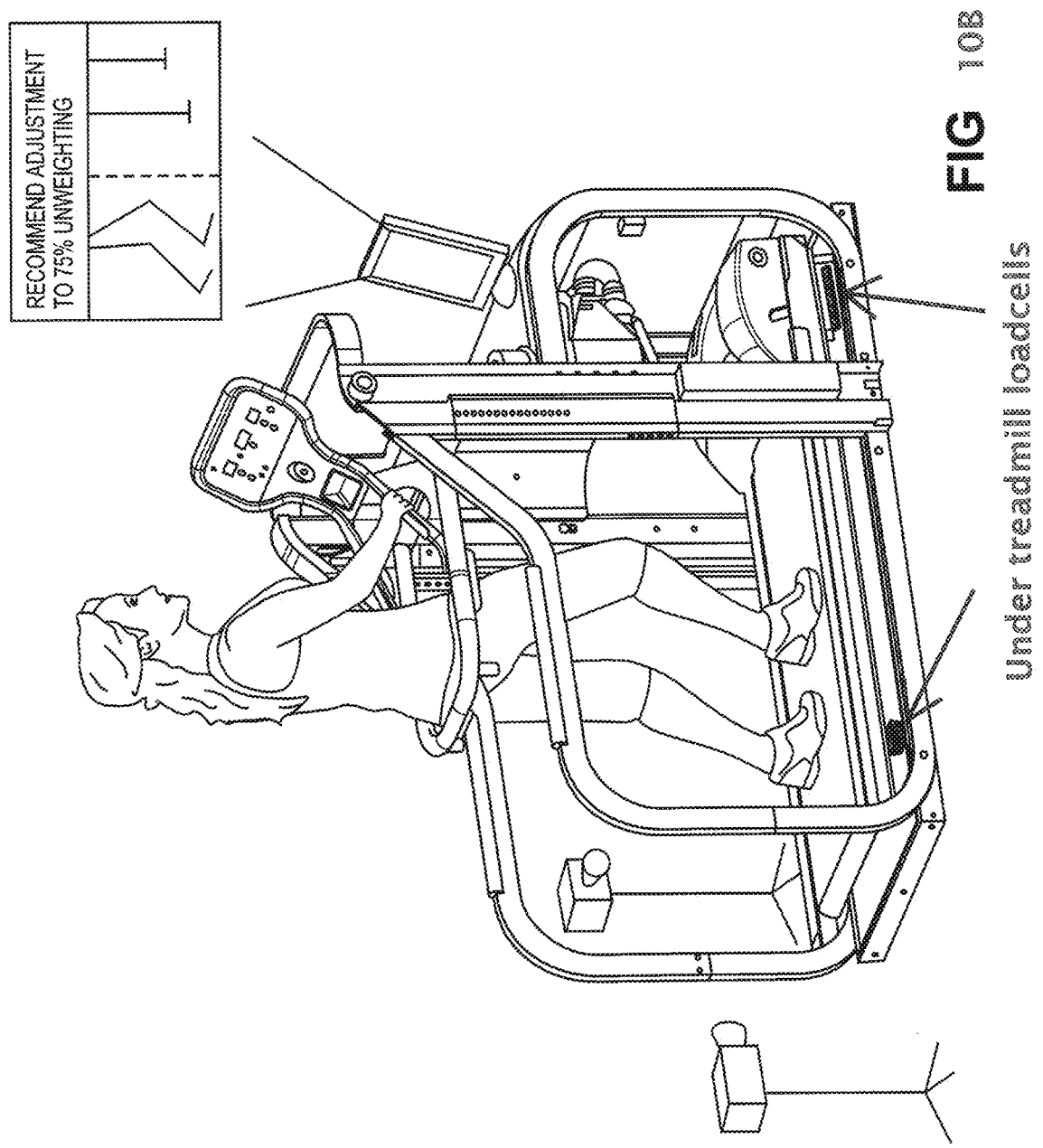
FIG. 10B is a perspective view of a user within a DAP chamber undergoing unweighted training similar to FIG. 10A. The DAP chamber bag is removed to show the interior. Unlike FIG. 10A, the user is not wearing markers or instrumented garments. All user gait data detected, recorded and synthesized is provided by the unweighting system load cells. There are two load cells shown underneath the treadmill frame within the DAP chamber base. Two other load cells on the opposite side are present but not visible in this view. The display associated with the unweighting system illustrates a gait parameter output or recommendation obtained using the load cell information and other information collected from the unweighting system.

FIGS. 10A and 10B illustrate differential air pressure systems with load cells positioned underneath the treadmill frame. FIG. 10A, for example, illustrates a patient a using a DAP system with load cells positioned underneath the treadmill frame. In this position, the weight of the DAP system is borne by the load cells. Two load cells are visible and two others (not shown) are positioned on the other side. Additionally, optional gait collection equipment is provided including cameras, ground force sensors, and inertial sensors on the user's legs and hips. In this view, the pressure bag that normally covers the frame and defines the pressure chamber is removed to permit the interior details of the pressure chamber and the instruments contained therein to be observed. Throughout the workout, the system takes data about the user's gait, speed, incline, and effective body-weight. That information is synthesized and given to the therapist during or at the end of the workout. In one alternative, the therapist can then watch a video that shows the patient's movements, speed, weighting, and the angles of the hips at each point. The therapist can use that information to more effectively set the next workout, leading to better recovery times. Due to the placement of the sensors, bio-mechanics points such as the user's hips, that are not visible through the enclosure of a current DAP system, can be measured, tracked and evaluated.

FIG. 10B illustrates one exemplary system using multiple gait analysis tools and DAP to provide real-time feedback to assist patients and therapists. The load cells are configured under the treadmill base as described above with FIG. 10A. In the view of FIG. 10B, the pressure bag that normally covers the frame and defines the pressure chamber is removed to permit the interior details of the pressure chamber and the instruments contained therein to be observed. To help the therapists identify better treatments, incorporating an analysis aspect into the first system would allow the therapists to receive real-time input on ways to improve the workout from a quantitative standpoint. The state of the art treatments now use either video feedback or force sensors with DAP to show the therapist or patient limited aspects of their gait. By integrating and synthesizing multiples sensors and measurement systems together, and providing analysis, the patients and therapists will be able to more accurately and thoroughly judge and correct or modify gait in a desired fashion.

It is to be appreciated that the various load cell improved systems described herein may be optionally extended to include feedback from other sensors used to capture gait, workout parameters, other physiological measurements, or psychological elements according to specific system, component, therapy or patient requirements. Integrating data from, for example, EEMG sensors and inertial sensors into understandable information would give a depth of information to a patient or therapist to adjust their gait with the assistance of unweighting that does not exist today. Further, in a DAP environment, such data is more useful to a patient and therapist than it would be in a full weight bearing environment because of the greater ability of the patient to adjust gait mechanics in the DAP environment. Similarly, the DAP environment permits greater ability to adjust gait desirably in response to these inputs than does an alternate environment such as pools or harness systems in which the gait measurements would be altered by the forces and restrictions placed on the user by the harness or pool environment and the ability of the user to adjust gait is less in such environments than in a DAP environment.

For additional details of these and other configurations of unweighting systems, refer to US Patent Application Publication US 2016/0007885, incorporated herein by reference in its entirety.

Figures 11, 12:
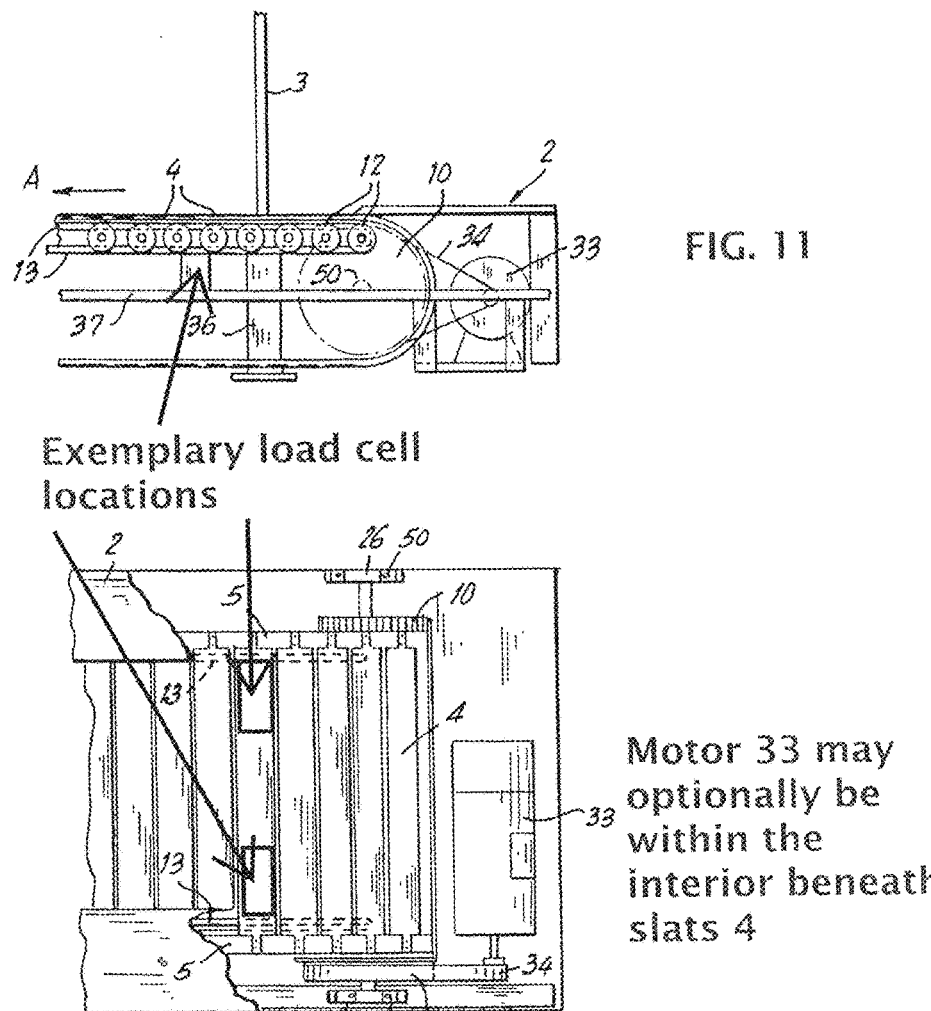
FIGS. 11 and 12 are a side view and a top down view, respectively, of a representative slat treadmill. Load cells locations shown are only exemplary and may be located in a number of possible locations to produce suitable load cell signals while taken specific treadmill designs into consideration when selecting a load cell mounting location.

Additionally, a slat style treadmill may be used in an unweighting system using the improved load cell applications and other improvements described herein. FIGS. 11 and 12 are a side view and a top down view, respectively, of a representative slat treadmill. Load cells locations shown are only exemplary and may be located in a number of possible locations to produce suitable load cell signals while taken specific treadmill designs into consideration when selecting a load cell mounting location. Illustrative load cell locations are identified in relation to the underlying slat belt support structure. The position of load cells will vary by slat belt design but are positioned to obtain user based interaction with the slats to obtain load cell gait information as described herein. The housing 2 includes frame members 36, 37 which provide for physical and structural support. Within the housing 2 are located rotatable drums, rollers, sleeves, sprockets or the like which the surface 1 which is a slat belt endless loop is placed. Additional details of the construction and alternative load cell positions with respect to a slat type treadmill will be appreciated with reference to U.S. Pat. Nos. 4,614,337; 6,348,025 and 5,577,598, each of which is incorporated by reference in its entirety.

It is to be appreciated that the DAP system control methods, including the various calibration techniques, include an offset based on the specific location of the DAP system load cells. The offset includes those factors that contribute to the accuracy of the load cell reading. Removing the weight of a treadmill frame or components of a DAP system may be required. In other circumstances, a vibration signal from a motor or moving belt may be removing from the load cell signals. In other instances, such as during DAP unweighting session performed on an inclined treadmill moving surface, the front pair of load cells may be removed from calculations. As such, in some embodiments, DAP load cell based gait measurements may be based on only rear pair load cell data.

FIG. 13 is a flow chart of a method 1300 of unweighting system calibration. First, at step 1305 a user is sealed into a differential air pressure (DAP) chamber. Next, at step 1310, DAP chamber pressure is increased to an initial DAP pressure level. Next, determine DAP weight from DAP system load cell readings at initial DAP pressure level (step 1315). Next, at step 1320, increase DAP chamber pressure by a pressure calibration increment. Next, at step 1325, record DAP system load cell readings for DAP chamber pressure at pressure calibration increment. Next, at step 1330, compared load cell output at DAP chamber pressure at pressure calibration increment to prior DAP chamber pressure at prior pressure calibration increment.

If the outcome of the compare step 1330 is "yes" (step 1337), the method continues by returning to step 1320 and increasing DAP chamber pressure by the selected pressure calibration increment.

If the outcome of the compare step 1330 is "no" (step 1339), the method continues by proceeding to step 1340 to determine user specific values such as a user specific calibration curve and a user specific maximum unweighting level for this DAP training session.

Finally, at step 1345, the user performs a DAP session on a DAP system controlled by the user specific information from the calibration method 1300. For example, there is now a user specific calibration curve that will be used to determine the appropriate DAP chamber pressure for a desired on waiting amount. In addition, there is now a user specific maximum unweighting level determined by the maximum amount of unweighting achieved or that user in that chamber and that DAP system configuration during that calibration session. Additionally, load cell information collected during the DAP training session may be used to provide gait information based on DAP system load cell information with, without, or based in part on factors determined during the above-mentioned calibration process.

FIG. 14 is a flow chart of a calibration method 1400 for a user specific differential air pressure chamber session. The method 1400 accommodates variation in user size as well as the ability of a user body shape to seal within the differential air pressure chamber. Furthermore, the specific geometry of a chamber cockpit as well as the user seal also contributes to variations in calibration methodology as well as results. If a user is a child (a pediatric user), then the weight of the user often less than 80 pounds is very small compared to the overall full range of the load cells. The typical full scale load cell range is from 0 to 1000 pounds. As a result, a pediatric user represents a very small load on the system. Additionally, for some user body types, there may also be a desire to set a maximum unweighting amount as well as to adjust the load cell gain and improve overall DAP chamber performance and responsiveness.

Similar to the method 1300, the method 1400 begins by the user being sealed into the DAP chamber (step 1405). Next, the initial DAP pressure level is provided to the chamber and recorded for this particular user similar to the method 1300. (Steps 1410 and 1415).

Next, the method 1400 considers whether to decrease load cell full-scale range for this user. (Step 1420). If the answer to step 1420 is "NO" (step 1435), the method 1400 proceeds to the user calibration steps described in the method 1300 and then proceeds to performing a DAP session based on calibration information (1440) as described above for the method 1300.

If the answer to step 1420 is "YES" (step 1425), the method 1400 proceeds to step 1445 to apply a gain and decrease load cell full-scale. Next, at step 1450, using the load cell reduced scale, proceed to perform calibration method 1300 and from step 1320. Additionally or optionally, at step 1455, designate a maximum DAP unweighting level for the user. This step may be added as an additional query in step 1335. As a result of such modification, this step included a determination of a change in the decreased full scale load cell output or a determination whether or not the designated maximum DAP unweighting level has been reached. Thereafter, using the determined calibration level using signals from the reduced full scale load cells, and the determined or designated maximum unweighting level, proceed to perform the DAP session according step 1460.

Advantageously, the methods 1300 and 1400 described above along with their alternatives enable user specific DAP chamber calibration for a wider range of users. Specifically, it is been observed that the introduction of the initial DAP chamber pressure provides a reliable baseline or a specific user, in a specific DAP chamber configuration for that specific DAP chamber cockpit and user seal position relative to the DAP system overall. Advantageously, the use of the initial DAP chamber pressure procedure appears to accommodate for a wide array of user session specific configurations such as user characteristics for that session, cockpit setting, cockpit height, user seal, user seal height, DAP chamber configuration, and DAP system configuration. Still further, the determination of the maximum unweighting level for a specific user is again tailored to the performance of the DAP system for that user with those specific configurations for that session. In some embodiments, the maximum unweighting level determined by the method 1300 is rounded up to the nearest 5% unweighting level. For example, if during the performance of method 1300 it was determined that a maximum unweighting level for a user was 53% then the system would record and provide to the user and limit operations of the DAP unweighting system to a maximum unweighting level of 55% for that user session. In the case of a pediatric user, the maximum unweighting level may be set for a different amount based on a safe unweighting range rather than the full unweighting capabilities of the DAP chamber system. By designating a maximum unweighting level, a system designed to unweighting a user up to several hundred pounds a then be fine-tuned to operate well and reliably and repeatedly within a much smaller weight range. In still other embodiments, the DAP load cells are sampled at a frequency of 100 Hz or 100 load cell samples per second. Gait parameters may be determined at a different interval. Gait parameters may be calculated every second. Gait parameters may be displayed or provided to the user. Gait parameters may be provided after a signal quality check such as a stride validation check.

Exemplary Computer System

Figure 15:
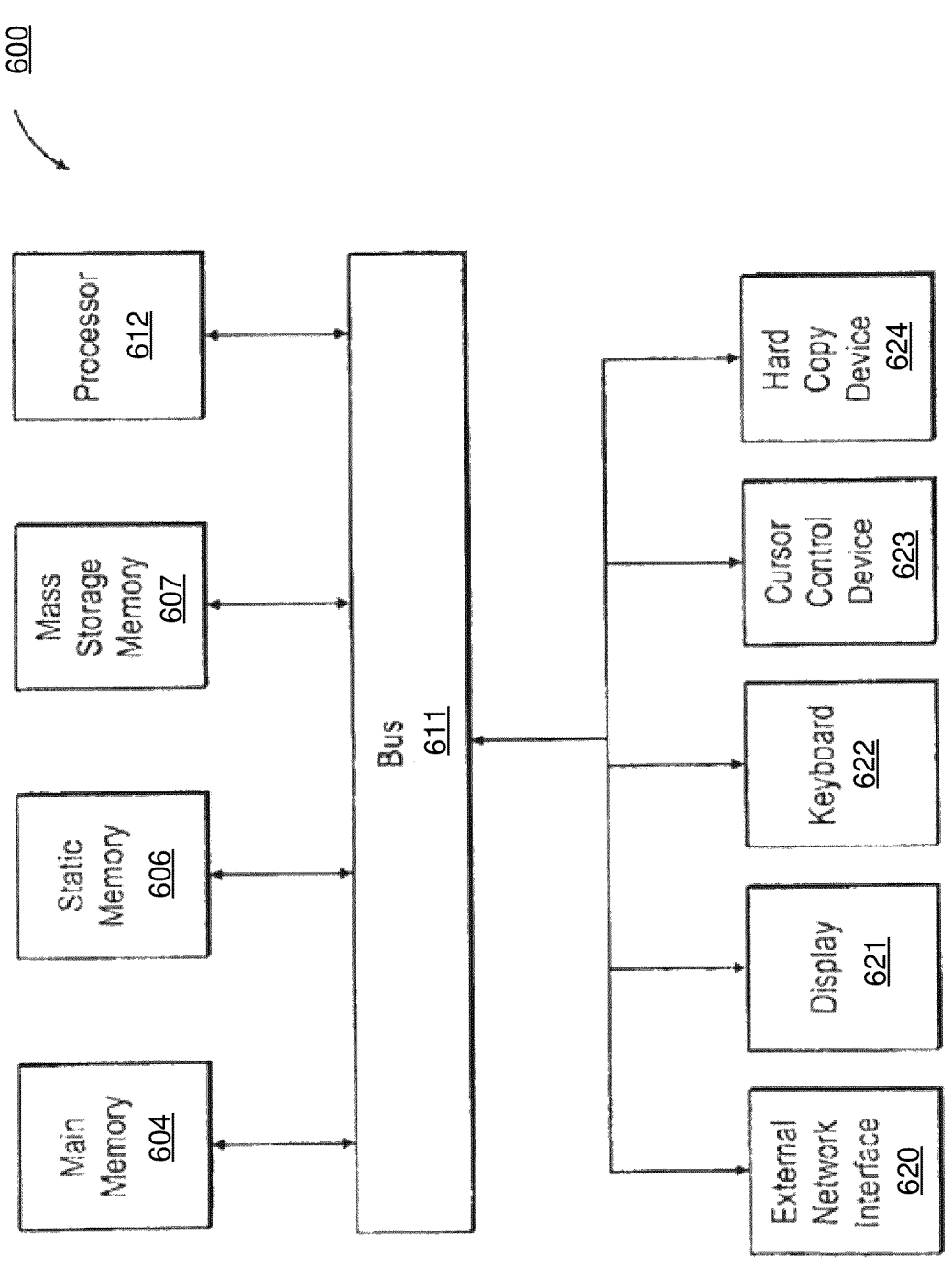
FIG. 15 is a schematic drawing of a representative computer controller for use in an unweighting system.

FIG. 15 is a block diagram of an exemplary computer system 600 adapted and configured to perform one or more of the logic, control, data collection, software and hardware operations and the like described herein. In some embodiments, the computer system also includes a software controlled gain adjustment for the load cells associated with an unweighting system. Still further, the computer system and electronic controls of an unweighting system may be adapted and configured to have computer readable instructions for implementing methods 1300 and 1400 described above. Still further, the computer system and electronic controls of an unweighting system may be adapted and configured to have computer readable instructions for controlling chamber pressure, treadmill speed, treadmill incline or other DAP system components according to factors and data obtained by performing the various steps of the methods 1300 and 1400 described above.

The computer system 600 may be adapted and configured using hardware, software, firmware in any combination, for example, to perform the various gait functions described herein as well as various other computer controlled and implemented methods. Additionally or optionally, the exemplary computer system 600 may also provide suitable electronic connections along with wired and wireless communication capabilities for direct and remote user interfaces, inputs and controls including touch screen, voice activated commands, remote control devices including those implemented using smart phones, tablets or mobile phones as well as other types of mobile graphical user interface devices. The computer system includes operating systems, software, firmware and communications for the use of the various user input devices described herein such as the touch screen interface, E-stop, user interface controls, interactive user interface and GUI display, touch button bar, as well as the various cameras and data recording devices.

The exemplary computer system 600 may comprise an exemplary client or server computer system. Computer system 600 comprises a communication mechanism or bus 611 for communicating information, and a processor 612 coupled with bus 611 for processing information. Processor 612 may in some variations be a microprocessor, but is not limited to a microprocessor.

System 600 further comprises a random access memory (RAM), or other dynamic storage device 604 (referred to as main memory) coupled to bus 611 for storing information and instructions to be executed by processor 612. Main memory 604 also may be used for storing temporary variables or other intermediate information during execution of instructions by processor 612.

Computer system 600 also comprises a read only memory (ROM) and/or other static storage device 606 coupled to bus 611 for storing static information and instructions for processor 612, and a data storage device 607, such as a magnetic disk or optical disk and its corresponding disk drive. Data storage device 607 is coupled to bus 611 for storing information and instructions.

Computer system 600 may further be coupled to a display device 621, such as a cathode ray tube (CRT) or liquid crystal display (LCD), coupled to bus 611 for displaying information to a computer user. An alphanumeric input device 622, including alphanumeric and other keys, may also be coupled to bus 611 for communicating information and command selections to processor 612. An additional user input device is cursor control 623, such as a mouse, trackball, trackpad, stylus, or cursor direction keys, coupled to bus 611 for communicating direction information and command selections to processor 612, and for controlling cursor movement on display 621.

Another device that may be coupled to bus 611 is hard copy device 624, which may be used for marking information on a medium such as paper, film, or similar types of media. Another device that may be coupled to bus 611 is a wired/wireless communication capability 625 to communication to a phone or handheld palm device, a LAN network, a remote network or a cloud based computer network or other distributed or shared computing and data storage system.

Note that any or all of the components of system 600 and associated hardware may be used in the inventive systems described herein. However, it can be appreciated that other configurations of the computer system 600 may include some or all of the devices. Certain variations of system 600 may include peripherals or components not illustrated in FIG. 15, e.g. components configured to receive different types of user input, such as audible input, or a touch sensor such as a touch screen.

Certain embodiments may be implemented as a computer program product that may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or another type of medium suitable for storing electronic instructions.

Additionally, some embodiments may be practiced in distributed computing environments where the machine-readable medium is stored on and/or executed by more than one computer system. In addition, the information transferred between computer systems may either be pulled or pushed across the communication medium connecting the computer systems.

The gait measurement methods, calibration and other unweighting system controls described herein along with digital processing device(s) described herein may include one or more general-purpose processing devices such as a microprocessor or central processing unit, a controller, or the like. Alternatively, the digital processing device may include one or more special-purpose processing devices such as a digital signal processor (DSP), an application specific integrated circuit (ASIC), a field programmable gate array (FPGA), or the like. In an alternative embodiment, for example, the digital processing device may be a network processor having multiple processors including a core unit and multiple microengines. Additionally, the digital processing device may include any combination of general-purpose processing device(s) and special-purpose processing device(s).

Networked System of Treadmill for Data Collection

A data collection and analysis system for use with unweighting systems is provided. Unweighting systems can be configured to capture data, such as a user's therapy history, goal, current condition, user type, age, medical history, etc. Analysis of an aggregate collection of such data from multiple users can allow an unweighting system or a therapist to generate a suggested treatment protocol or adapt a protocol already in use. Additionally, analysis of an aggregate collection of data can indicate whether certain assessments are indicated, such as a gait, balance, or concussion assessment. Such assessments collect data indicative of impairments from the user. This data can be compared against a normal threshold range, which can be generated from aggregate user data.

Figure 16:
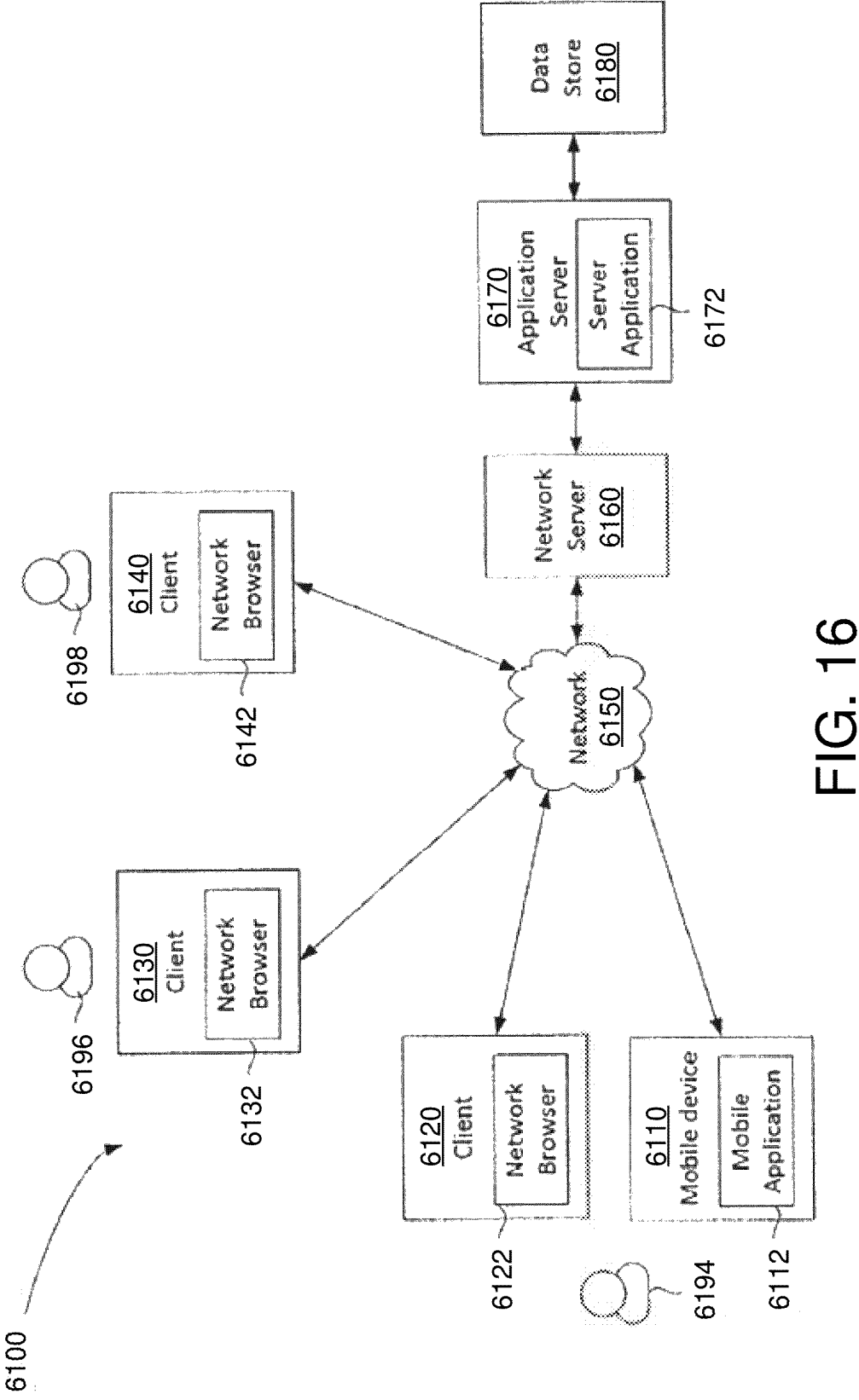
FIG. 16 illustrates a networked communications system to implement the various embodiments of cloud connected unweighting systems.

FIG. 16 is a block diagram of an exemplary networked computer system to implement the various embodiments of a cloud connected treadmill control system such as, for example, systems including a user and provider authentication structure enabling a medical professional supervising a patient session or an individual performing an unsupervised session. Additionally or optionally, the system includes the inventive security and data management system and methods to enable the use of the system as a medical professional, in a medical setting, where a patient record is being created or found within a cloud connected system where search functions and data transmission are central to functionality.

System 6100 of FIG. 16 includes mobile device 6110 and client device 6120 associated with user 6194, network 6150, network server 6160, application servers 6170, and data store 6180. The system of FIG. 16 also includes client 6130 for physician or healthcare provider 6196 and client 6140 for third party 6198. Though the discussion below may refer to a physician, a healthcare provider and a physical therapist are intended to be interchangeable for purposes of explaining the methods and systems disclosed herein.

In some embodiments, a method of unweighting system treatment management is provided. The method comprises providing a user's information, the information comprising at least two of the following characteristics: age, weight, gender, location, desired result, current medical condition, height, lift access requirements, therapist access requirements, therapy history, past workout information, and user type, wherein user type comprises at least one of an athlete, a casual user, a rehabilitation user, and a chronic user; analyzing, using a processor, the user's information based, at least in part, on aggregate information in a database comprising other users' characteristics and associated past workout session data including duration, speed, incline, and unweighting level used during workouts; and generating, using a processor, a suggested workout routine including duration, speed, incline, and unweighting level to be used during a workout based on the comparing of the user's information to the other users' information.

Mobile device 6110 may communicate with network 6150 via any suitable wired or wireless communication method and includes mobile application 6112. Mobile device 6110 may include an instrumented medical treadmill or an unweighting training system as described herein including mechanical unweighting systems and differential air pressure systems. Mobile device 6110 may receive input from a user and execute one or more programs to administer one or more tests, exercise routines, challenges, prescribed protocols, recommended protocols including unweighting therapy protocols and recommendations to a user, provide test results to application server 6170, and receive test set data, account data, and other data from application server 6170. The user may be a patient of a physician associated client 6130. The terms user and patient may be used interchangeably herein for purposes of explaining the operation of the system 6100. Mobile application 6112 resides in memory on mobile device 6110 and may be executed to allow a user to setup and login to an account with a network service, establish goals, get feedback, review and update or administer test results, and perform other functions related to unweighted therapy or gait evaluation or sharing of load cell based calibration data for one or more users.

Client device 6120 may include network browser 6122 and be implemented as a computing device, such as for example a laptop, tablet, mobile phone, smart phone, desktop, workstation, or some other suitable computing device. Network browser 6122 may be a client application for viewing content provided by an application server, such as application server 6170 via network server 6160 over network 6150.

Network 6150 may facilitate communication of data between different servers, devices and machines. The network may be implemented as a private network, cloud based network, distributed network, public network, intranet, the Internet, or a combination of these networks. Network server 6160 is connected to network 6150 and may receive and process requests received over network 6150. Network server 6160 may be implemented as one or more servers implementing a network service. When network 6150 is the Internet, network server 6160 may be implemented as one or more web servers. The network 150 may also be a cloud computing network.

Application server 6170 communicates with network server 6160 via network server 6160 and data store 6180. Application server 6170 may also communicate with other machines, wearable devices, biometric measurement devices and gait devices as described herein. Application server 6170 may host a server application 6172, and other software modules. Application server 6170 may be implemented as one server or multiple servers. Server application 6172 may reside on application server 6170 and may be executed to store, retrieve and transmit test set data, analyze test set results, and manage alerts.

Data store 6180 may be accessed by application server 6170. Data store 6170 may store data, process data, and return queries received from application server. Data stored on application data store 6180 may include user account data, user test data, user test results, analysis of the results such as trend data, and other data.

Clients 6130 and 6140 and network browsers 6132 and 6142 may be similar to client 6120 and network browser 6122, except that clients 6130 and 6140 may be associated with a physician and a third party, respectively, rather than a user (patient). Exemplary third parties include, for example, a drug company, a joint prosthesis company or manufacturer, a health care payer, an accountable care organization, an insurance company, a physical therapist, an athletic trainer or a hospital.

Figure 17:
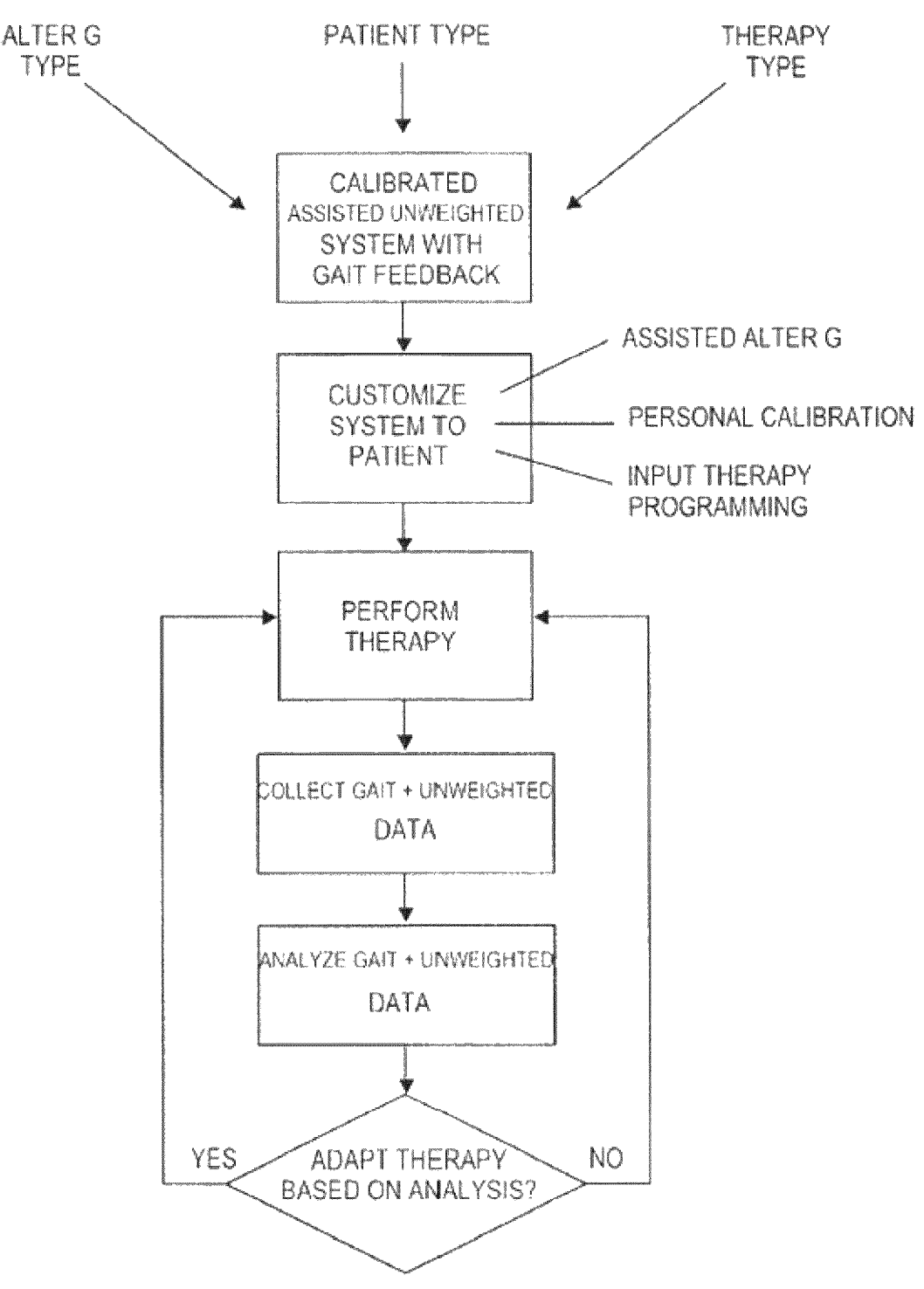
FIG. 17 is an exemplary method of providing unweighting therapy using an unweighting system having improved load cell utilization and unweighted gait parameters.

FIG. 17 is an exemplary method of providing therapy for patient using a differential pressure having measured gait feedback capabilities.

First, with an understanding of the different types of unweighting systems available, the patient type to use the system, and the desired therapy to be performed, select an appropriate system to perform therapy with a user. For example, focusing on DAP systems, a number of systems types for categories 1, 2 and 3 are provided in the '124 application. A category 1 system includes for example FIG. 2A of the '124 application. A category 2 system includes for example FIG. 7A of the '124 application. A category 3 system includes for example FIG. 1A and 19 of the '124 application. A category 4 system includes for example FIG. 19A of the '307 Application.

Next, customize the system to this patient. Customization may take on many forms such as based on the specific type or configuration of the unweighting system being used, personal calibration techniques, or inputs of specific patient parameters, or protocols or patient specific training goals.

Next, the user performs the therapy in the system according to the input program or protocol.

Next, the system will collect gait and unweighting and other system parameters while therapy is ongoing.

Next, the system will analyze the collected data.

Next, determine whether to adapt the therapy based on the prior analysis step. One result of this step is to adapt the therapy and continue to perform the therapy as adapted. Another result is to continue to perform therapy without adapting the therapy based on the analysis.

Figure 18:
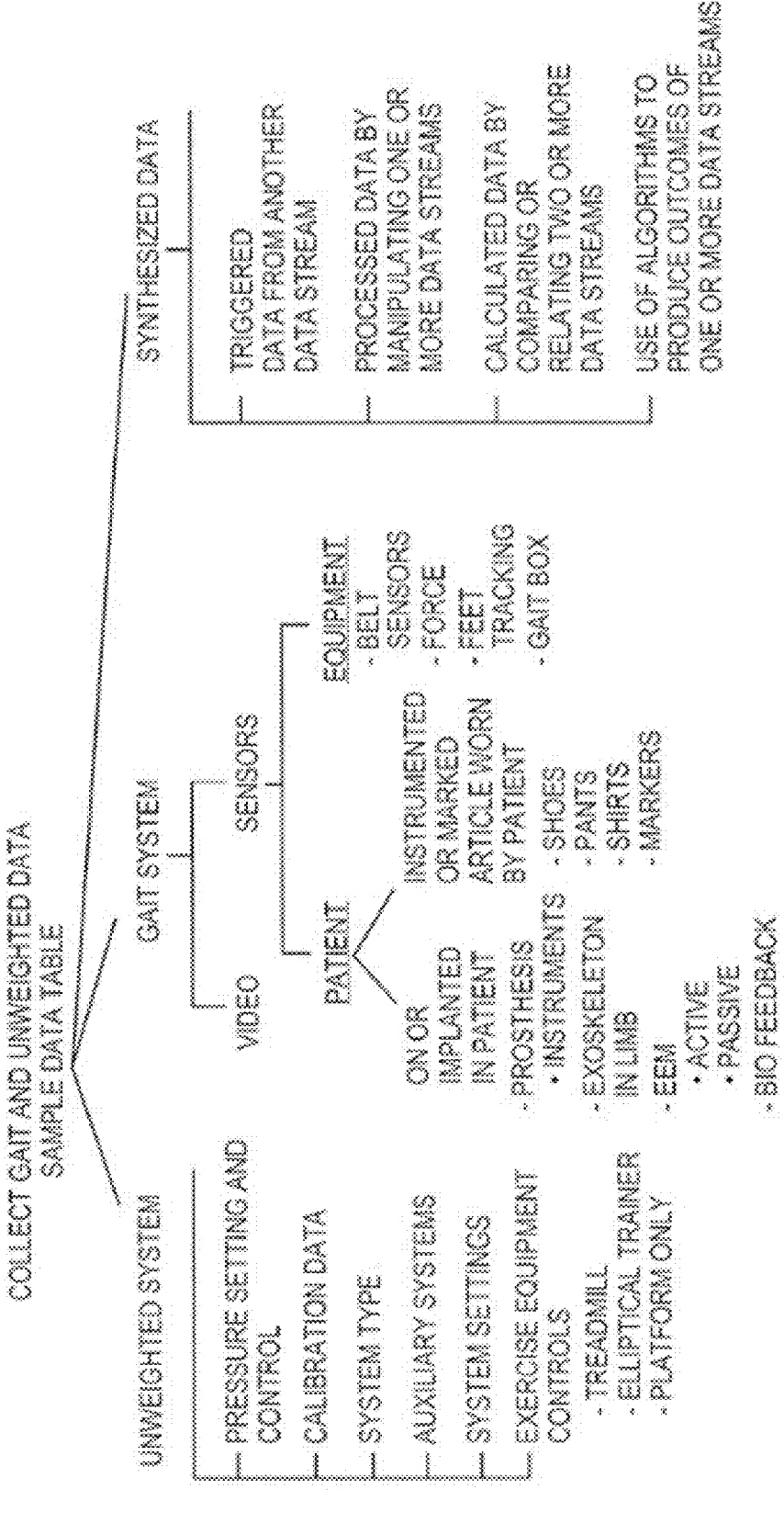
FIG. 18 is an exemplary data table showing the various data streams that may be collected and synthesized including those from pediatric users and including data based on improved unweighted load cell techniques for calibration, gait parameters, maximum unweighting level or gain adjusted unweighting load cells.

One example of the format of a data table for an integrated differential air pressure and gait measuring and training device is shown in FIG. 18. This representative data system envisions collection and synthesis of data from several data streams depending upon the specific configuration of the system being used for therapy. The contents of FIG. 18 (i.e., the data table or variables collected, controlled, processed or manipulated by the control system) will vary to the degree needed to include collection of the various continuous, nearly continuous or segmented data streams including synthesized data from the therapy system.

Simultaneous data collection refers to the general process of collecting data from multiple data streams under a common time stamp. It is to be appreciated that embodiments of the various inventive unweighting gait training systems described herein are adapted and configured for this purpose. However, the various inventive systems are also adapted and configured to synthesize the data that is being collected from the systems, subsystems, accessories, and sensors as shown in the exemplary data table (See FIG. 18). As used herein, synthesis of data refers to the integration of the independent data streams collected into another set of data or stream of data used in conjunction with the therapy or training undertaken in the system. Synthesis goes beyond basic data collection in that the data is put together to straight-forwardly assist the patient or therapist understand the workout from a quantitative standpoint. Data collection systems just record data, but do not take steps towards helping a patient or therapist who do not have training or experience with the direct data being collected. In one alternative, the type of data synthesis is derived from the type of patient receiving therapy and the specific system selected for his patient category (i.e., class 1, 2, 3 or 4). As such, the type of patient or system is one factor in determining the type of data synthesis needed for a specific patient therapy session or course of therapy. In still further alternatives, the data collected from one component is used to indicate the relevance of a subset of data from another source. In one specific example, there is a camera providing a high definition video stream of a post knee surgery patient's knee movement during therapy. The storage and later processing requirement for such a high volume of data may be a difficult and time consuming task. In one specific example of data synthesis, a force sensor on a treadmill is used to indicate heel strike and triggers the capture of a video stream that runs for a set time limit. In another specific embodiment, there is also a loop recorder used in conjunction with the high definition video stream. In this example, the heel strike sensor, employed in conjunction with a timing offset, is used to trigger the capture of a portion of the high definition stream in the loop just prior to the heel strike reading. Thereafter, the data stream is stored for an additional timing factor after heel strike. During the use of this data, the relevant portion of the video is now cut down to and synchronized with the recording or relevant trigger, here a heel strike reading in this example. In one example, the selective combination of heel strike data with video stream data to represent the collection of frame grab or snippet of unweighting and gait data. The data or data stream can be presented in real time, or packaged in a way to inform a doctor, therapist, shoe maker, etc. of the state of the patient.

In still other aspects of the various embodiments described herein, the system processor or controller of an integrated gait training system or the processor of a self-contained biometric sensor system contains computer readable instructions adapted and configured for storing, in a computer readable database stored within or accessible to the processor, the collected, synchronized or synthesized data of the unweighting system and the gait system. In some aspects, the collected, synchronized or synthesized data includes, depending upon system configuration and therapy performed data of one or more of: pressure setting and control, calibration data, system type, auxiliary systems, exercise system controls, video, user worn sensor or equipment sensor, synthesized data triggered from another data stream, synthesized data from processed data from manipulating one or more data streams, synthesized data calculated by comparing or relating two or more data streams, or, optionally, synthesized data obtained using algorithms to produce outcomes of one or more data streams. In still other aspects, collected, synchronized or synthesized data is displayed, output or provided to provide real-time feedback to a user of the system. In still further aspects, there are computer readable instructions for synthesizing the system by integration of independent data streams collected into another set of data or stream of data used in conjunction with the therapy or training performed using the system. In still other aspects, collected, synchronized or synthesized data is derived from the type of patient receiving therapy and the specific system selected for his patient category (i.e., class 1, 2 or 3). In some aspects, the type of patient or system is one factor in determining the type of data synthesis applied to a specific patient therapy session or course of therapy. In still other aspects, collected, synchronized or synthesized data from one component is used to indicate the relevance of a subset of data from another component or source. It is to be appreciated that the resulting data or data stream can be presented in real time, or packaged in a way to inform another person or system or process of the state of the patient.

In still other embodiments any of the above systems or methods are performed on cloud connected medical treadmill software system having a treadmill exercise system having a computer controller with a computer readable memory medium and computer controlling instructions within the memory; the computer readable memory medium containing one or more software applications having computer readable instructions for performing a function within the memory of the computer controller or via communication with a remote server to perform one or more of: authenticating a user to access patient information on a touch-screen interface in communication with the treadmill exercise system; searching for a particular patient using one or more patient search features adapted and configured for preventing the identification of other patients or users stored in the memory accessible to the treadmill exercise system or for preventing the display of protected health information of other patients or users.

In one aspect of the above embodiments performed using a medical treadmill system, one or more software applications is configured to collectively perform one or more of the steps of: establishing a patient profile; entering protected health information from the patient, searching for existing patient records with patient identification shielding, initiating an exercise therapy or diagnostic session with said patient; displaying real-time or near real-time treadmill metrics and analysis tools; or collecting treadmill session data and communicating to remote server.

In general, in one embodiment, an integrated differential air pressure assisted gait training system includes a differential air pressure system having a computer controller, at least one gait measurement or indication system in communication with the computer controller, and a computer readable database stored within or accessible to the computer controller comprising collected DAP system data from the differential air pressure system and gait system data from the at least one gait measurement or indication system This and other embodiments can include one or more of the following features. In one aspect, the DAP system data can include one or more of pressure setting and control, calibration data, system type, auxiliary systems, exercise system controls. In another aspect, the gait system data can include video, user worn sensor or equipment sensor. In a further aspect, the computer readable database can further include synthesized data from at least one of unweighted system data or gait system data. In an alternative aspect, the synthesized data can be triggered from another data stream. In still another aspect, the synthesized data can be processed data by manipulating one or more data streams. In one aspect, the synthesized data can be calculated data by comparing or relating two or more data streams. In another aspect, the synthesized data can include using algorithms to produce outcomes of one or more data streams. In a further aspect, can further include a display in communication with the computer controller adapted and can be configured to provide real-time feedback to a user of the differential air pressure system. In an alternative aspect, the system can further include video input in database. In yet another aspect, the video data stored can be collected based on a trigger from another component or device of the integrated system. In still another aspect, the database can be accessible to computer controller or accessible to the controller via wired or wireless communication. In one aspect, the system can include at least one gait measurement or indication system and can further include an enclosure, a pair of sensors supported by the enclosure and positioned such that when the enclosure is coupled to a treadmill of the integrated unweighting system a portion of the tread can be within the detectable range of the pair of sensors, and a processor supported by the enclosure and in communication with the pair of sensors and having computer readable instructions to receive and process an output from the pair of sensors and to perform calculations related to obtaining gait parameters based on the input from the sensors.

In general, in one embodiment, a method of training an individual to improve or alter walking or running mechanics by unweighting includes preparing the individual for training in a differential air pressure environment provided by a differential air pressure system, performing a training routine with the individual to improve or alter walking or running mechanics while the user is experiencing unweighting by the differential air pressure system, simultaneously measuring one or more of a user gait parameter or a user biomechanical parameter during the performing step, and collecting the one or more measured user gait parameter or measured user biomechanical parameter under instructions from a controller of the differential air pressure system.

In some embodiments, a method of using an unweighting system is provided. The method comprises downloading a workout routine to an unweighting system, the workout routine comprising a desired duration, speed, incline, and level of unweighting; identifying a user to the unweighting system; performing the workout routine; and recording performance data during the workout routine in the unweighting system. The method can further comprise connecting the unweighting system to a network. The method can further comprise uploading the performance data to the network. The method can further comprise providing user or therapist feedback to the unweighting system. User feedback can comprise feedback regarding at least one of satisfaction with the workout routine, overall mood and level of pain. Therapist feedback can comprise at least one of observations of the workout routine and rating of user progress. In some embodiments, identifying the user comprises providing user information or providing an identifier configured to access user information through the unweighting system. An appropriate workout routine can be selected based on user information. In some embodiments, the appropriate workout routine is selected based on reviewing past workout routines and performance data of other users sharing one or more user characteristics. The method can further comprise adjusting the downloaded workout routine. The method can further comprise sending performance data to at least one of a doctor, and insurance provider, and a patient file. The method can further comprise sending at least one of performance data, user feedback, and therapist feedback to an aggregate user database. In some embodiments, the method further comprises adjusting future unweighting workouts based on the performance data, user feedback, or technician feedback. The method can further comprise assessing user performance after a workout session to determine whether to modify workout parameters or scheduling.

In general, in one embodiment, an integrated unweighted gait training system, includes an unweighting system comprising a computer controller, a gait measurement system in communication with the controller, and a display in communication with the computer controller adapted and configured to provide real-time feedback to a user of the integrated unweighting gait training system.

This and other embodiments can include one or more of the following features. In one aspect, the unweighting system can be a differential air pressure unweighting system. In another aspect, the unweighting system can be a non-DAP unweighting system. In a further aspect, the non-DAP unweighting system can be a support frame type non-DAP unweighting system. In an alternative aspect, the non-DAP unweighting system can be a curved arch type non-DAP unweighting system. In yet another aspect, the non-DAP unweighting system can be an unweighting arch type non-DAP unweighting system. In still another aspect, the non-DAP unweighting system can be a monocolumn type non-DAP unweighing system. In one aspect, the non-DAP unweighting system can be a cantilevered type non-DAP unweighting system. In another aspect, the gait measurement system can further include an enclosure, a pair of sensors supported by the enclosure and positioned such that when the enclosure is coupled to a treadmill of the integrated unweighting system a portion of the tread is within the detectable range of the pair of sensors, and a processor in communication with the pair of sensors and having computer readable instructions to receive and process an output from the pair of sensors and to perform calculations related to obtaining gait parameters based on the input from the sensors. In a further aspect, the processor can perform calculations to obtain tread belt speed, time of foot impact and left/right foot indication.

In still other alternatives, one or more of the following methods of training is modified based on an aspect of the improved unweighting provided by the improved load cell operations describe herein. In general, in one embodiment, a method of training an individual to improve or alter walking or running mechanics by unweighting includes preparing the individual for training in a differential air pressure environment provided by a differential air pressure system, performing a training routine with the individual to improve or alter walking or running mechanics while the user is experiencing unweighting by the differential air pressure system, simultaneously measuring one or more of a user gait parameter or a user biomechanical parameter during the performing step, and collecting the one or more measured user gait parameter or measured user biomechanical parameter under instructions from a controller of the differential air pressure system.

In still other alternatives, one or more of the following methods of training or system operations is modified based on an aspect of the improved unweighting provided by the improved load cell operations describe herein. In one aspect, the DAP system data can include one or more of pressure setting and control, calibration data, system type, auxiliary systems, exercise system controls. In another aspect, the gait system data can include video, user worn sensor or equipment sensor. In a further aspect, the computer readable database can further include synthesized data from at least one of unweighted system data or gait system data. In an alternative aspect, the synthesized data can be triggered from another data stream. In still another aspect, the synthesized data can be processed data by manipulating one or more data streams. In one aspect, the synthesized data can be calculated data by comparing or relating two or more data streams. In another aspect, the synthesized data can include using algorithms to produce outcomes of one or more data streams. In a further aspect, can further include a display in communication with the computer controller adapted and can be configured to provide real-time feedback to a user of the differential air pressure system. In an alternative aspect, the system can further include video input in database. In yet another aspect, the video data stored can be collected based on a trigger from another component or device of the integrated system. In still another aspect, the database can be accessible to computer controller or accessible to the controller via wired or wireless communication. In one aspect, the system can include at least one gait measurement or indication system and can further include an enclosure, a pair of sensors supported by the enclosure and positioned such that when the enclosure is coupled to a treadmill of the integrated unweighting system a portion of the tread can be within the detectable range of the pair of sensors, and a processor supported by the enclosure and in communication with the pair of sensors and having computer readable instructions to receive and process an output from the pair of sensors and to perform calculations related to obtaining gait parameters based on the input from the sensors.

This and other embodiments can include one or more of the following features.

In one aspect, the operations of the integrated system during a user therapy session can include at least one user action recommendation or system control function related to using synthesized data.

In another aspect, the at least one action related to control using synthesized data can include the use of unweighting system data or gait system data triggered from another data stream.

In a further aspect, the at least one action related to control using synthesized data can include the use of processed unweighting system data or gait system data by manipulating one or more data streams.

In an alternative aspect, the at least one action related to control using synthesized data can include the use of calculated unweighting system data or gait system data produced by comparing or relating two or more data streams.

In yet another aspect, the at least one action related to control using synthesized data can include the use of algorithms to produce outcomes of one or more unweighting system data streams or gait system data streams Additional modifications to unweighting training are also provided by implementing the improved use of load cell information for calibration of and operation of a DAP unweighting system. Examples of improved methods include, in one embodiment, a method of providing integrated unweighting assisted gait training for a user having impaired walking biomechanics includes unweighting the user in an appropriate unweighting system, performing a therapy routine with the user, collecting data under control of a controller or a computer processor of the appropriate unweighting system from a plurality of components of the integrated differential air pressure system during the unweighting step and the performing step, and analyzing one or more of the output data from the collecting step to determine whether to adapt the performing step. Thereafter, determining to adapt the performing step wherein an adaptive step or an adjustment step comes from a therapist, from the system or as part of a data controlled therapy. In still other aspects, the step of analyzing is done by person or by the controller of an unweighting system. Still further, after the analyzing step, optionally, there follows a step of continuing the performing step without adapting the therapy routine. Still further, after the analyzing step there follows a step of continuing the performing step after adapting the therapy routine. Other optional steps include: providing the user with feedback regarding how the user's impaired walking biomechanics are changing; repeating the unweighting, performing, collecting and analyzing steps to progressively re-train the user for walking or running with proper biomechanics; or repeating the unweighting, performing, collecting and analyzing steps to progressively proceed from a partial unweighting environment during the unweighting step to a full weight bearing environment during the unweighting step.

Additional modifications to unweighting training are also provided by implementing the improved use of load cell information for calibration of and operation of a DAP unweighting system. Examples of improved methods include, in one aspect, the unweighting step can be adapted and configured to provide a partial unweighting environment specific to the rehabilitation of a patient diagnosed with a disease or an injury. In another aspect, the unweighting environment can be adjusted to achieve a symmetrical walking pattern for the patient. In a further aspect, the unweighted environment can be adjusted by the user. In an alternative aspect, the unweighted environment can be adjusted by the differential air pressure system according to a predetermined protocol. In yet another aspect, the collecting step can be initiated by detecting a heel strike and triggering a video stream capture.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

Any of the embodiments and load cell configurations summarized herein may be the basis of one or more additional alternative embodiments of unweighting systems using one or more of the improvements described herein such as: Stride Smart software, improved DAP system controls including enhanced PID controls, data streaming, cloud collection of raw or processed data, or use of treadmill based load cells In some embodiments, a method of unweighting system treatment management is provided. The method comprises providing a user's information, the information comprising at least two of the following characteristics: age, weight, gender, location, desired result, current medical condition, height, lift access requirements, therapist access requirements, therapy history, past workout information, and user type, wherein user type comprises at least one of an athlete, a casual user, a rehabilitation user, and a chronic user; analyzing, using a processor, the user's information based, at least in part, on aggregate information in a database comprising other users' characteristics and associated past workout session data including duration, speed, incline, and unweighting level used during workouts; and generating, using a processor, a suggested workout routine including duration, speed, incline, and unweighting level to be used during a workout based on the comparing of the user's information to the other users' information.

The analyzing can comprise comprising matching user characteristics to other users' characteristics. Providing the user's information can comprise prioritizing at least one of the characteristics. The matching step can further comprise a) determining whether at least a portion of the user's characteristics matches at least a subset of at least one user's of the other users characteristics; b) omitting a lowest priority characteristic from the at least a portion of the user's characteristics to create a prioritized user information set if step a produces no match using the at least a portion of the user's characteristics; c) determining whether the prioritized user information set matches at least a subset of at least one user's of the other users characteristics; and d) repeating steps b and c until the prioritized user information matches at least a subset of the at least one user's characteristics. In some embodiments, analyzing comprises identifying at least one other user sharing characteristics with the user and having a favorable workout outcome. The favorable workout outcome can comprise at least one of user satisfaction, obtaining the desired result and progress towards the desired result. Current medical condition can comprise at least one of original diagnosis, dates of injuries, date or type of illness, date or type of interventions, an indication of rehabilitation progress, and a previous treatment and date of treatment. In some embodiments, therapy history comprises prescribed therapy history, actual therapy history, therapy history on an unweighting system, therapy history using other equipment. The method can further comprise generating a recommended therapy or workout based on a medical guideline. In some embodiments, providing the user's information occurs at a same appointment or workout session as the analyzing and generating steps. In some embodiments, providing the user's information occurs at an earlier appointment or workout session as the analyzing and generating steps. Providing the user's information can comprise creating a user profile or presenting a unique identifier. The method can further comprise sending the suggested workout routine to a medical professional or insurance provider for approval. The method can further comprise modifying, by the medical professional or insurance provider, the suggested workout routine. In some embodiments, the generating step comprising generating more than one suggested workout routines. The method can further comprise transferring funds from the user to a treatment facility or provider. The method can further comprise providing a cost for the suggested workout routine. Differential pricing can be used to determine the cost. The method can further comprise providing a list of unweighting systems appropriate for the suggested workout routine. The method can further comprise providing available appointment times for suitable unweighting systems. The method can further comprise scheduling an appointment. In some embodiments, generating a suggested workout routine comprises generating workout routine on equipment other than an unweighting system. The method can further comprise uploading the suggested workout routine to the database. The method can further comprise performing the suggested workout and uploading performance data to the database. In some embodiments, the method comprises an iterative process, generating periodic updates for the user or a medical professional. The method can further comprise generating subsequent suggested workout routines based on user progress.

In some embodiments, a system for unweighting usage management is provided. The system comprises a storage database comprising past user information and related workout data; a user interface allowing a present user to access information from or add information to the storage database, the information comprising at least two of the following characteristics: age, weight, gender, location, desired result, current medical condition, height, lift access requirements, therapist access requirements, therapy history, past workout information, and user type, wherein user type comprises at least one of an athlete, a casual user, a rehabilitation user, and a chronic user; a processor comprising instructions for comparing present user information and past user information and related workout data and generating a suggested workout routine including suggested duration, speed, incline, and unweighting to be used during a workout based on the comparing of the present user information to the past user information and related workout data.

The system can be configured to connect to one or more unweighting systems. The storage database can comprise a centralized or cloud based database. In some embodiments, the user interface can be accessed through a network interface such as an internet or LAN, a local terminal, laptop, tablet, computer, or smart phone. The system can comprise instructions for sending the suggested workout routine to a particular unweighting system, a medical professional, or an insurance provider.

In some embodiments, a method of finding an available and appropriate unweighting system site is provided. The method comprises identifying a user; providing a user location; providing one or more user system characteristics to identify an appropriate unweighting system, the user system characteristics comprising at least one of a user type, the user type comprising at least one of an athlete, a casual user, a rehabilitation user, and a chronic user, a medical condition, a desired result, and an unweighting system access need; matching, using a processor, the user system characteristics with one or more appropriate unweighting systems based on unweighting system features comprising type of unweighting system, unweighting provided, access provided, and analysis capability; and generating, using a processor, one or more suggested unweighting system sites based on compatibility of the unweighting system sites with the user location and the one or more appropriate unweighting systems.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of providing a user specific calibrated differential air pressure exercise session, comprising:
   sealing a user within a chamber of a differential air pressure system;
   inflating the chamber;
   increasing a speed of a moving belt of a treadmill in the chamber such that the user is walking within the chamber while the user is being unweighted by air pressure in the chamber;
   collecting data from a first load cell and a second load cell in differential air pressure system;
   determining a user specific unweighting calibration based on the collected data; and
   operating the differential air pressure system to unweight the user according to the user specific unweighting calibration.

2. The method of claim 1, wherein collecting data includes successively changing air pressure in the chamber and collecting data from the first load cell and the second load cell associated with the successive air pressures.

3. The method of claim 2, wherein the user specific unweighting calibration is based on a linear interpolation between two successive air pressures.

4. The method of claim 2, wherein a difference in an unweighting level between successive unweighting levels is 1% unweighting.

5. The method of claim 1, wherein collecting data includes collecting at least 50 successive air pressure and load cell measurements.

6. The method of claim 1, wherein a starting air pressure of the chamber is 60 mm of H2O.

7. The method of claim 1, wherein the first load cell is disposed under a first rear corner of the treadmill; and the second load cell disposed under a second rear corner of the treadmill.

8. The method of claim 1, further comprising adjusting air pressure in the chamber based on signals from one or more load cells.

9. The method of claim 1, wherein the user is unweighted by not less than 20% of body weight.

10. The method of claim 1, wherein a final unweighting level used in generating the user specific unweighting calibration curve is collected at a 40% unweighting level.

* * * * *